(12) United States Patent
Kodandaramaiah et al.

(10) Patent No.: US 11,866,687 B2
(45) Date of Patent: Jan. 9, 2024

(54) ROBOTIC PLATFORM FOR HIGH THROUGHPUT INJECTIONS INTO INTACT TISSUE

(71) Applicants: Regents of the University of Minnesota, Minneapolis, MN (US); Max-Planck-Gesellschaft zur Foerderung der Wissenschaften e.V., Munich (DE)

(72) Inventors: Suhasa Kodandaramaiah, Minneapolis, MN (US); Elena Taverna, Dresden (DE); Gabriella Shull, Minneapolis, MN (US); Wieland Huttner, Dresden (DE)

(73) Assignee: Regents of the University of Minnesota, Minneapolis, MN (US)

( * ) Notice: Subject to any disclaimer, the term of this patent is extended or adjusted under 35 U.S.C. 154(b) by 968 days.

(21) Appl. No.: 16/642,986

(22) PCT Filed: Sep. 6, 2018

(86) PCT No.: PCT/US2018/049728
§ 371 (c)(1),
(2) Date: Feb. 28, 2020

(87) PCT Pub. No.: WO2019/051072
PCT Pub. Date: Mar. 14, 2019

(65) Prior Publication Data
US 2020/0308531 A1    Oct. 1, 2020

Related U.S. Application Data

(60) Provisional application No. 62/554,993, filed on Sep. 6, 2017.

(51) Int. Cl.
*G01N 35/00* (2006.01)
*C12M 1/36* (2006.01)
(Continued)

(52) U.S. Cl.
CPC ........... *C12M 41/48* (2013.01); *B01L 3/0237* (2013.01); *B01L 9/54* (2013.01); *C12M 21/08* (2013.01);
(Continued)

(58) Field of Classification Search
CPC ...... C12M 41/48; C12M 41/08; C12M 41/40; C12M 21/08; C12M 23/16; C12M 23/50;
(Continued)

(56) References Cited

U.S. PATENT DOCUMENTS 7,881,533 B2 * 2/2011 Ando ............... G01N 35/1009
382/181
8,173,415 B2    5/2012 Noori et al.
(Continued)

FOREIGN PATENT DOCUMENTS

WO    2008/034249 A1    3/2008

OTHER PUBLICATIONS

Alegria et al., "Single neuron recording: progress towards high-throughput analysis," Future Medicine Ltd, Bioelectronics in Medicine, vol. 3, No. 3, doi: 10.2217/bem-2020-0011, Sep. 17, 2020, pp. 33-36.
(Continued)

*Primary Examiner* — Khai M Nguyen
(74) *Attorney, Agent, or Firm* — Shumaker & Sieffert, P.A.

(57) ABSTRACT

Techniques are described for automated microinjection of substances, such as genetic material, into single cells in tissue samples. An example system comprises a robotic manipulator apparatus configured to hold and position a micropipette. Furthermore, the system comprises a microscope camera positioned to observe an injection site. A computing device receives image data from a microscope camera of the system, where the image data represents an
(Continued)

image of a tissue sample. The computing device receives, via a user interface, an indication of a line traced by a user on the image of a tissue sample. In response, the computing device controls the robotic manipulator apparatus to move a tip of the micropipette along a path defined by the trajectory line. The pressure controller injects a gas into the micropipette to eject a substance out of the micropipette at one or more points along the path defined by the trajectory line.

18 Claims, 17 Drawing Sheets

(51) Int. Cl.
 C12M 3/00 (2006.01)
 C12M 3/06 (2006.01)
 C12M 1/00 (2006.01)
 C12M 1/26 (2006.01)
 C12M 1/34 (2006.01)
 G01N 35/10 (2006.01)
 B01L 3/02 (2006.01)
 B01L 9/00 (2006.01)
 C12N 15/87 (2006.01)
 C12N 15/89 (2006.01)

(52) U.S. Cl.
 CPC ............ *C12M 23/16* (2013.01); *C12M 23/50* (2013.01); *C12M 33/04* (2013.01); *C12M 41/08* (2013.01); *C12M 41/40* (2013.01); *G01N 35/00693* (2013.01); *G01N 35/109* (2013.01); *C12N 15/87* (2013.01); *C12N 15/89* (2013.01); *G01N 35/1002* (2013.01); *G01N 2035/1039* (2013.01)

(58) Field of Classification Search
 CPC ......... C12M 33/04; B01L 3/0237; B01L 9/54; G01N 35/00693; G01N 35/109; G01N 35/1002; G01N 2035/1039; C12N 15/87; C12N 15/89
 See application file for complete search history.

(56) References Cited

U.S. PATENT DOCUMENTS

| | | | |
|---|---|---|---|
| 8,990,023 | B2 | 3/2015 | Sun et al. |
| 9,668,804 | B2 | 6/2017 | Kodandaramaiah et al. |
| 10,596,541 | B2 | 3/2020 | Weitz et al. |
| 11,712,549 | B2 * | 8/2023 | Rand ...................... B33Y 10/00 604/46 |
| 2008/0077329 | A1 * | 3/2008 | Sun ......................... C12M 23/50 702/19 |
| 2011/0027885 | A1 * | 2/2011 | Sun ......................... C12N 15/89 435/375 |
| 2012/0225435 | A1 | 9/2012 | Seger et al. |
| 2016/0051353 | A1 | 2/2016 | Yanik et al. |
| 2019/0127782 | A1 | 5/2019 | Regev et al. |
| 2020/0308531 | A1 | 10/2020 | Kodandaramaiah et al. |
| 2022/0309705 | A1 | 9/2022 | Kodandaramaiah et al. |

OTHER PUBLICATIONS

Annecchino et al., "Robotic Automation of In Vivo Two-Photon Targeted Whole-Cell Patch-Clamp Electrophysiology," Neuron, vol. 95, No. 5, Aug. 2017, pp. 1048-1055.
Bassett et al., Highly Efficient Targeted Mutagenesis of *Drosophila* with the CRISPR/Cas9 System, Cell Reports, vol. 4, No. 1, Jul. 2013, pp. 220-228.
Behjati et al., "What is Next Generation Sequencing?," Arch. Dis. Child. Educ. Pract. Ed., vol. 98, No. 6, Dec. 2013, pp. 236-238.
Cadwell et al., "Electrophysiological, Transcriptomic and Morphologic Profiling of Single Neurons using Patch-Seq," Nat. Biotechnol., vol. 34, No. 2, Feb. 2016, 19 pp.
Canny, "A Computational Approach to Edge Detection," IEEE Transactions on Pattern Analysis and Machine Intelligence , vol. 8, No. 6, doi: 10.1109/TPAMI.1986.4767851, Dec. 1986, pp. 679-698.
Dean, "Microinjection," Brenner's Encyclopedia of Genetics, 2nd Edition, vol. 4, doi:10.1016/8978-0-12-374984-0.00945-1, May 2013, pp. 409-410.
Delpiano et al., "Automated Detection of Fluorescent Cells In In-Resin Fluorescence Sections for Integrated Light and Electron Microscopy," J. Microsc., vol. 271, No. 1, pp. 109-119, Jul. 2018.
Delubac et al., "Microfluidic system with integrated microinjector for automated *Drosophila* embryo injection," The Royal Society of Chemistry, Lab Chip, vol. 12, DOI: 10.1039/c21c40104e, Sep. 2012, pp. 4911-4919.
Dietzl et al., "A genome-wide transgenic RNAi library for conditional gene inactivation in *Drosophila*," Nature, vol. 448, No. 7150, doi: 10.1038/nature05954, Jul. 2007, pp. 151-157.
Fitzharris et al., "Electrical-assisted microinjection for analysis of fertilization and cell division in mammalian oocytes and early embryos [Chapter 19]," Elsevier Inc., Methods in Cell Biology, 1st ed., vol. 144, https://doi.org/10.1016/bs.mcb.2018.03.036, May 2018, pp. 431-440.
Gompel et al., "*Drosophila* germline transformation," retrieved from http://gompel.org/wp-content/uploads/2015/12/Drosophila-transformation-with-chorion.pdf, Oct. 2015, 11 pp.
Gong et al., "Ends-out, or replacement, gene targeting in *Drosophila*," Proceedings of the National Academy of Sciences, PNAS, vol. 100, No. 5, Mar. 2003, pp. 2556-2561.
Gonzalez et al., "Machine Learning-Based Pipette Positional Correction for Automatic Patch Clamp In Vitro," eNeuro, vol. 8, No. 4, Jul. 2021, 8 pp.
Gratz et al., "Genome Engineering of *Drosophila* with the CRISPR RNA-Guided Cas9 Nuclease," Genetics Society of America, Genetics, vol. 194, No. 4, Aug. 2013, pp. 1029-1035.
Gurcan et al., "Histopathological Image Analysis: A Review," IEEE Rev. Biomed. Eng., vol. 2, Oct. 30, 2009, pp. 147-171.
Harder et al., "Automated Analysis of the Mitotic Phases of Human Cells in 3D Fluorescence Microscopy Image Sequences," in Medical Image Computing and Computer-Assisted Intervention— MICCAI 2006, Feb. 2006, pp. 840-848.
Holst et al., "Autonomous Patch-Clamp Robot for Functional Characterization of Neurons in Vivo: Development and Application to Mouse Visual Cortex," J. Neurophysiol., vol. 121, No. 6, Jun. 2019, pp. 2341-2357.
Hwang et al., "Single-Cell RNA Sequencing Technologies and Bioinformatics Pipelines," Exp. Mol. Med., vol. 50, No. 8, Aug. 2018, 14 pp.
Irshad et al., "Methods for Nuclei Detection, Segmentation, and Classification in Digital Histopathology: A Review—Current Status and Future Potential," IEEE Rev. Biomed. Eng., vol. 7, May 2014, pp. 97-114.
Khosla et al., "Gold Nanorod Induced Warming of Embryos from Cryogenic State Enhances Viability," American Chemical Society, ACS Nano, vol. 11, No. 8, doi: 10.1021/acsnano.7602216, Jul. 2017, pp. 7869-7878.
Kim et al., "A functional genomic screen for cardiogenic genes using RNA interference in developing *Drosophila* embryos," Proceedings of the National Academy of Sciences, PNAS, vol. 101, No. 1, Jan. 2004, pp. 159-164.
Kimmel et al., "Stages of Embryonic Development of the Zebrafish," Wiley-Liss, Inc., Developmental Dynamics, vol. 203, No. 3, doi: 10.1002/aja.1002030302, Jul. 1995, pp. 253-310.
Kolb et al., "PatcherBot: a Single-Cell Electrophysiology Robot for Adherent Cells and Brain Slices," J. Neural Eng., vol. 16, No. 4, Aug. 2019, 13 pp.
Koos et al., "Automatic Deep Learning-Driven Label-Free Image-Guided Patch Clamp System," Nat. Commun., vol. 12, No. 1, Feb. 2021, 12 pp.
Lawson et al., "In Vivo Imaging of Embryonic Vascular Development Using Trasngenic Zebrafish, " Developmental Biology, vol. 248, No. 2, doi: 10.1006/dbio.2002.0711, Aug. 2002, pp. 307-318.

(56) References Cited

OTHER PUBLICATIONS

Lee et al., "Development of a transient expression assay for detecting environmental oestrogens in zebrafish and medaka embryos," BMC Biotechnology, vol. 12, No. 32, doi: 10.1186/1472-6750-12-32, Jun. 2012, pp. 1-12.
Li et al., "A Robot for High Yield Electrophysiology and Morphology of Single Neurons in Vivo," Nat. Commun., vol. 8, No. 1, Jun. 2017, 10 pp.
Mateos-Pérez et al., "Comparative Evaluation of Autofocus Algorithms for a Real-Time System for Automatic Detection of *Mycobacterium tuberculosis*," Cytometry A, vol. 81A, No. 3, Jan. 2012, pp. 213-221.
Nan et al., "Depth Detection for a Stereo Cell Micro-injection System with Dual Cameras," 2017 IEEE International Conference on Robotics and Biomimetics, ROBIO 2017, doi:10.1109/ROBIO.2017.8324565, Dec. 5-8, 2017, pp. 1-6.
Pech-Pacheco et al., "Diatom autofocusing in brightfield microscopy: a comparative study," IEEE, Proceedings 15th International Conference on Pattern Recognition. ICPR-2000, vol. 3, doi: 10.1109/ICPR.2000.903548, Feb. 2000, pp. 314-317.
Pertuz et al., "Analysis of Focus Measure Operators for Shape-From-Focus," Pattern Recognit., vol. 46, No. 5, May 2013, pp. 1415-1432.
Ren et al., "Faster R-CNN: Towards Real-Time Object Detection with Region Proposal Networks," arXiv, accessed from https://arxiv.org/abs/1506.01497v1, Jun. 2015, 10 pp.
Ringrose et al., "Chapter 1—Transgenesis in *Drosophila melanogaster*," Transgenesis Techniques, Methods in Molecular Biology, vol. 561, doi: 10.1007/978-1-60327-019-9, (Applicant points out, in accordance with MPEP 609.04(a), that the year of publication, 2009, is sufficiently earlier than the effective U.S. filing date, so that the particular month of publication is not in issue.), 2009, pp. 3-19.
Rosen et al., "Microinjection of Zebrafish Embroys to Analyze Gene Function," Journal of Visualized Experiments and Gene Tools, vol. 25, e1115, doi:10.3791/1115, Mar. 2009, 5 pp.
Rubin et al., "Genetic Transformation of *Drosophila* with Transposable Element Vectors," Science, vol. 218, No. 4570, Oct. 1982, pp. 348-353.
Schubert et al., "Microinjection into zebrafish embryos (*Danio rerio*)—a useful tool in aquatic toxicity testing?," Environmental Sciences Europe, vol. 26, No. 32, doi: 10.1186/s12302-014-0032-3, Dec. 2014, 9 pp.
Shull et al., "Manipulation of Single Neural Stem Cells and Neurons in Brain Slices using RObotic Microinjection," JOVE, jove.com/video/61599, vol. 167, e61599, doi: 10.3791/61599, Jan. 2021, pp. 1-15.
Shull et al., "Robotic platform for microinjection into single cells in brain tissue," EMBO Reports, vol. 20, No. 10, e47880, doi:10.15252/embr.201947880, Aug. 2019, pp. 1-16.
Simon, "Optimal State Estimation: Kalman, H Infinity, and Nonlinear Approaches," John Wiley & Sons, 2006 (Applicant points out, in accordance with MPEP 609.04(a), that the year of publication, 2006, is sufficiently earlier than the effective U.S. filing date, so that the particular month of publication is not in issue.), 530 pp.
Spradling et al., "Transposition of Cloned P Elements into *Drosophila* Germ Line Chromosomes," Science, vol. 218, No. 4570, doi:10.1126/science.6289435, Oct. 22, 1982, pp. 341-347.
Sreedhar et al., "Enhancement of Images Using Morphological Transformations," International Journal of Computer Science & Information Technology (IJCSIT), vol. 4, No. 1, DOI : 10.5121/ijcsit.2012.4103, Feb. 2012, pp. 33-50.
Stahl et al., "Visualization and Analysis of Gene Expression in Tissue Sections by Spatial Transcriptomics," Science, vol. 353, No. 6294, Jul. 2016, pp. 78-82.
Suk et al., "Closed-Loop Real-Time Imaging Enables Fully Automated Cell-Targeted Patch-Clamp Neural Recording In Vivo," Cell Press, Neuron, vol. 95, No. 5, doi: 10.1016/j.neuron.2017.08.011, Aug. 2017, pp. 1037-1047.
Sun et al., "Autofocusing in Computer Microscopy: Selecting the Optimal Focus Algorithm," Microscopy Research and Technique, vol. 65, Oct. 2005, pp. 139-149.
U.S. Appl. No. 17/935,494, filed Sep. 26, 2022, naming inventors Kodandaramaiah et al.
Venken et al., "Genetic Manipulation of Genes and Cells in the Nervous System of the Fruit Fly," Cell Press, Neuron, vol. 72, No. 2, doi: 10.1016/j.neuron.2011.09.021, Oct. 2011, pp. 202-230.
Xu, "Chapter 10—Visual Servo Control with Force Regulation for Microinjection," Springer International Publishing AG, Micromachines for Biological Micromanipulation, doi.org/10.1007/978-3-319-74621-0_10, Feb. 3, 2018, pp. 209-223.
Yip et al., "Deep Learning-Based Real-Time Detection of Neurons in Brain Slices for in Vitro Physiology," Sci. Rep., vol. 11, No. 1, Mar. 2021, 10 pp.
Zappe et al., "Automated MEMS-based *Drosophila* embryo injection system for high-throughput RNAi screens," The Royal Society of Chemistry, Lab Chip, vol. 6, DOI: 10.1039/b600238b, Jun. 2006, pp. 1012-1019.
Zhao et al., "A Review of Automated Microinjection of Zebrafish Embryos," MDPI, Micromachines, vol. 10, No. 7, doi: 10.3390/mi10010007, Dec. 24, 2018, 26 pp.
Abramoff et al., "Image Processing with ImageJ," Biophotonics International, vol. 11, No. 7, Jul. 2004, 7 pp.
Arnold et al., "The T-box transcription factor Eomes/Tbr2 regulates neurogenesis in the cortical subventricular zone," Genes & Development, vol. 22, No. 18, Jul. 2008, 6 pp.
Attardo et al., "Live Imaging at the Onset of Cortical Neurogenesis Reveals Differential Appearance of the Neuronal Phenotype in Apical versus Basal Progenitor Progeny," PLoS ONE, vol. 3, No. 6, Jun. 2008, 16 pp.
Bahrey et al., "Voltage-gated Currents, Dye and Electrical Coupling in the Embryonic Mouse Neocortex," Cerebral Cortex, vol. 13, No. 3, Mar. 2003, 13 pp.
Becattini et al., "A Fully Automated System for Adherent Cells Microinjection," IEEE Journal of Biomedical and Health Informatics, vol. 18, No. 1, Jan. 2014, 11 pp.
Caccamo et al., "An Immunohistochemical Characterization of the Primitive and Maturing Neuroepithelial Components in the OTT-6050 Transplantable Mouse Teratoma," Neuropathology and Applied Neurobiology, vol. 15: Mar. 1989, 17 pp.
Chang et al., "Organ-Targeted High-Throughput In Vivo Biologics Screen Identifies Materials for RNA Delivery," Integrative Biology: Quantitative Biosciences from Nano to Macro, vol. 6, No. 10, Oct. 2014, 17 pp.
Chow et al., "A High-Throughput Automated Microinjection System for Human Cells With Small Size," IEEE/ASME Transactions on Mechatronics, vol. 21, No. 2, Apr. 2016, 13 pp.
Clavaguera et al., "Transmission and spreading of tauopathy in transgenic mouse brain," Nature Cell Biology, vol. 11, No. 7, Jul. 2009, 15 pp.
Costa et al., "Continuous live imaging of adult neural stem cell division and lineage progression in vitro," Development (Cambridge, England), vol. 138, No. 6, Mar. 2011, 12 pp.
Farkas et al., "The cell biology of neural stem and progenitor cells and its significance for their proliferation versus differentiation during mammalian brain development," Current Opinion in Cell Biology, vol. 20, No. 6, Dec. 2008, 9 pp.
Florio et al., "A single splice site mutation in human-specific ARHGAP11B causes basal progenitor amplification," Science Advances, vol. 2, No. 12, Dec. 2016, 8 pp.
Kalebic et al., "CRISPR/Cas9-induced disruption of gene expression in mouse embryonic brain and single neural stem cells in vivo," EMBO Reports, vol. 17, No. 3, Jan. 2016, 11 pp.
Kodandaramaiah et al., "Automated whole-cell patch-clamp electrophysiology of neurons in vivo," Nature Methods, vol. 9, No. 6, Jun. 2012, 13 pp.
Kodandaramaiah et al., "Multi-neuron intracellular recording in vivo via interacting autopatching robots," eLife, vol. 7, Jan. 2018, 19 pp.
Kodandaramaiah et al., "Setting up and using the autopatcher for automated intracellular neural recording in vivo," Nature Protocols, vol. 11, No. 4, Apr. 2016, 44 pp.

(56) References Cited

OTHER PUBLICATIONS

Lacar et al., "Gap junction-mediated calcium waves define communication networks among murine postnatal neural progenitor cells," European Journal of Neuroscience, vol. 34, No. 12, Dec. 2011, 16 pp.
Liu et al., "Gap Junctions/Hemichannels Modulate Interkinetic Nuclear Migration in the Forebrain Precursor,". Journal of Neuroscience, vol. 30, No. 12, Mar. 2010, 13 pp.
Lui et al., "Development and Evolution of the Human Neocortex," Cell, vol. 146, No. 1, Jul. 2011, 19 pp.
Millman et al., "Python for Scientists and Engineers," Computing in Science & Engineering, vol. 13, Mar./Apr. 2011, 4pp.
Miyata et al., "Asymmetric production of surface-dividing and non-surface-dividing cortical progenitor cells," Development (Cambridge, England), vol. 131, No. 13, Jul. 2004, 13 pp.
Molotkov et al., "Gene Delivery to Postnatal Rat Brain by Nonventricular Plasmid Injection and Electroporation," Journal of Visualized Experiments, vol. 43, Sep. 2010, 4 pp.
Permana et al., "A Review of Automated Microinjection Systems for Single Cells in the Embryogenesis Stage," IEEE/ASME Transactions on Mechatronics, vol. 21, No. 5, Oct. 2016, 14 pp.
Rakic, P., "Evolution of the neocortex: a perspective from developmental biology," Nature Reviews Neuroscience, vol. 10, No. 10, Oct. 2009, 28 pp.
Savall et al., "Dexterous robotic manipulation of alert adult *Drosophila* for high-content experimentation," Nature Methods, vol. 12, No. 7, Jul. 2015, 13 pp.
Schindelin et al., "Fiji: an open-source platform for biological-image analysis," Nature Methods, vol. 9, No. 7, Jul. 2012, 7 pp.
Schwamborn et al., "The sequential activity of the GTPases Rap1B and Cdc42 determines neuronal polarity," Nature Neuroscience, vol. 7, No. 9, Aug. 2004, 7 pp.
Suk et al., "Closed-Loop Real-Time Imaging Enables Fully Automated Cell-Targeted Patch-Clamp Neural Recording In Vivo," Neuron, vol. 95, No. 5, Aug. 2017, 21 pp.
Sun et al., "Biological Cell Injection Using an Autonomous MicroRobotic System," The International Journal of Robotics Research, vol. 21, No. 10-11, Oct.-Nov. 2002, 8 pp.
Takahashi et al., "Manipulating gene expressions by electroporation in the developing brain of mammalian embryos," Differentiation, vol. 70, No. 4-5, Jun. 2002, 8 pp.
Tavano et al., "Insm1 Induces Neural Progenitor Delamination in Developing Neocortex via Downregulation of the Adherens Junction Belt-Specific Protein Plekha7," Neuron, vol. 97, Mar. 2018, 39 pp.
Taverna et al., "A new approach to manipulate the fate of single neural stem cells in tissue," Nature neuroscience, vol. 15, No. 2, Dec. 2011, 11 pp.
Wong et al., "Microinjection of membrane-impermeable molecules into single neural stem cells in brain tissue," Nature Protocols, vol. 9, No. 5, Apr. 2014, 13 pp.
Wu et al., "Integration of autopatching with automated pipette and cell detection in vitro," Journal of Neurophysiology, vol. 116, No. 4, Oct. 2016, 15 pp.
"Ogshull/Autoinjector" retrieved from https://github.com/ogshull/Autoinjector—on Jul. 22, 2020, 7 pp.
"Scripy.interpolate.UnivariateSpline." SciPy: Open Source Scientific Tools for Python, retrieved from https://docs.scipy.org/doc/scipy/reference/generated/scipy.interpolate.UnivariateSpline.html, on Jul. 22, 2020, 3 pp.
Communication Pursuant to Rules 161(1) and 162 EPC from counterpart European Application No. 18778731.2, dated Apr. 16, 2020, 3 pp.
International Search Report and Written Opinion of International Application No. PCT/US2018/049728, dated Dec. 19, 2018, 15 pp.
International Preliminary Report on Patentability from International Application No. PCT/US2018/049728, dated Mar. 19, 2020, 8 pp.
Office Action from counterpart European Application No. 18778731.2, dated Mar. 29, 2021, 4 pp.
Asp et al., "Spatially Resolved Transcriptomes—Next Generation Tools for Tissue Exploration," BioEssays, vol. 42, No. 10, May 4, 2020, 16 pp.
Long et al., "3D Image-Guided Automatic Pipette Positioning for Single Cell Experiments in Vivo," Scientific Reports, vol. 5, No. 1, Dec. 2015. 8 pp.
O'Brien, "Improved Computer Vision Algorithms for High-Throughput Targeting of Single Cells in Intact Tissue for Automated Microinjections," University of Minnesota, Oct. 2021, 148 pp.
Stoeckius et al., "Cell Hashing with Barcoded Antibodies Enables Multiplexing and Doublet Detection for Single Cell Genomics," Genome Biology, vol. 19, No. 224, Dec. 19, 2018, 12 pp.

\* cited by examiner

ROBOTIC PLATFORM FOR HIGH THROUGHPUT INJECTIONS INTO INTACT TISSUE

This application is a National Stage application under 35 U.S.C. § 371 of PCT Application No. PCT/US2018/049728, entitled "ROBOTIC PLATFORM FOR HIGH THROUGHPUT INJECTIONS INTO INTACT TISSUE" and filed on Sep. 6, 2018, which claims the benefit of U.S. Provisional Patent Application No. 62/554,993, titled "ROBOTIC PLATFORM FOR HIGH THROUGHPUT SINGLE CELL GENE MANIPULATION IN INTACT TISSUE" and filed Sep. 6, 2017. The entire contents of application nos. PCT/US2018/049728 and 62/554,993 are incorporated herein by reference.

GOVERNMENT INTEREST

This invention was made with government support under NS103098 awarded by National Institutes of Health. The government has certain rights in the invention.

TECHNICAL FIELD

The disclosure relates to equipment for microinjection of substances into cells.

BACKGROUND

Manual microinjection enables scientists to inject single cells with molecules or other substances of interest in order to investigate cell decision making, cell differentiation, and other biological processes. Other methods of delivery of biological components into cells in tissues include viral delivery and electroporation.

SUMMARY

This disclosure describes automated microinjection of substances, such as genetic material, into single cells in tissue samples, such as intact tissue. For example, techniques are described that enable automating the process of injecting controlled solutions into cells using an autoinjector that includes a custom pressure controller, such as a 3-axis manipulator controlled by user input, and computer-vision feedback. The techniques may achieve increased yield with an increased total number of attempts in similar or less amount of time as compared to manual injection.

In one example, this disclosure describes a system for injecting a substance into cells of a tissue sample. The system comprises a robotic manipulator apparatus configured to hold and position a micropipette. The system also comprises a pressure controller. Additionally, the system comprises a microscope camera. A computing device of the system may be configured to receive image data from the microscope camera. The image data comprises an image of the tissue sample. Additionally, the computing device may output a user interface for display. The user interface contains the image of the tissue sample. Additionally, the computing device may receive, via the user interface, an indication of user input of a trajectory line drawn by a user on the image of the tissue sample. The computing device may control the robotic manipulator apparatus to move a tip of the micropipette along a path defined by the trajectory line. Additionally, the computing device may control the pressure controller to inject the gas into the micropipette to eject the substance out of the micropipette at one or more points along the path defined by the trajectory line.

In another example, this disclosure describes a method performed by a system for injecting one or more substances into cells of a tissue sample, the method comprising: receiving image data from a microscope camera, wherein the image data comprises an image of the tissue sample; outputting a user interface for display, wherein the user interface contains the image of the tissue sample; receiving, via the user interface, an indication of user input of a trajectory line drawn by a user on the image of the tissue sample; controlling a robotic manipulator apparatus to move a tip of the micropipette along a path defined by the trajectory line; and controlling a pressure controller to inject a gas into the micropipette to eject the substance out of the micropipette at one or more points along the path defined by the trajectory line.

In another example, this disclosure describes a computer-readable storage medium having instructions stored thereon that, when executed, cause a computing device of an autoinjector system to: receive image data from a microscope camera, wherein the image data comprises an image of a tissue sample; output a user interface for display, wherein the user interface contains the image of the tissue sample; receive, via the user interface, an indication of user input of a trajectory line drawn by a user on the image of the tissue sample; control a robotic manipulator apparatus to move a tip of the micropipette along a path defined by the trajectory line; and control a pressure controller to inject a gas into the micropipette to eject a substance out of the micropipette at one or more points along the path defined by the trajectory line.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1:
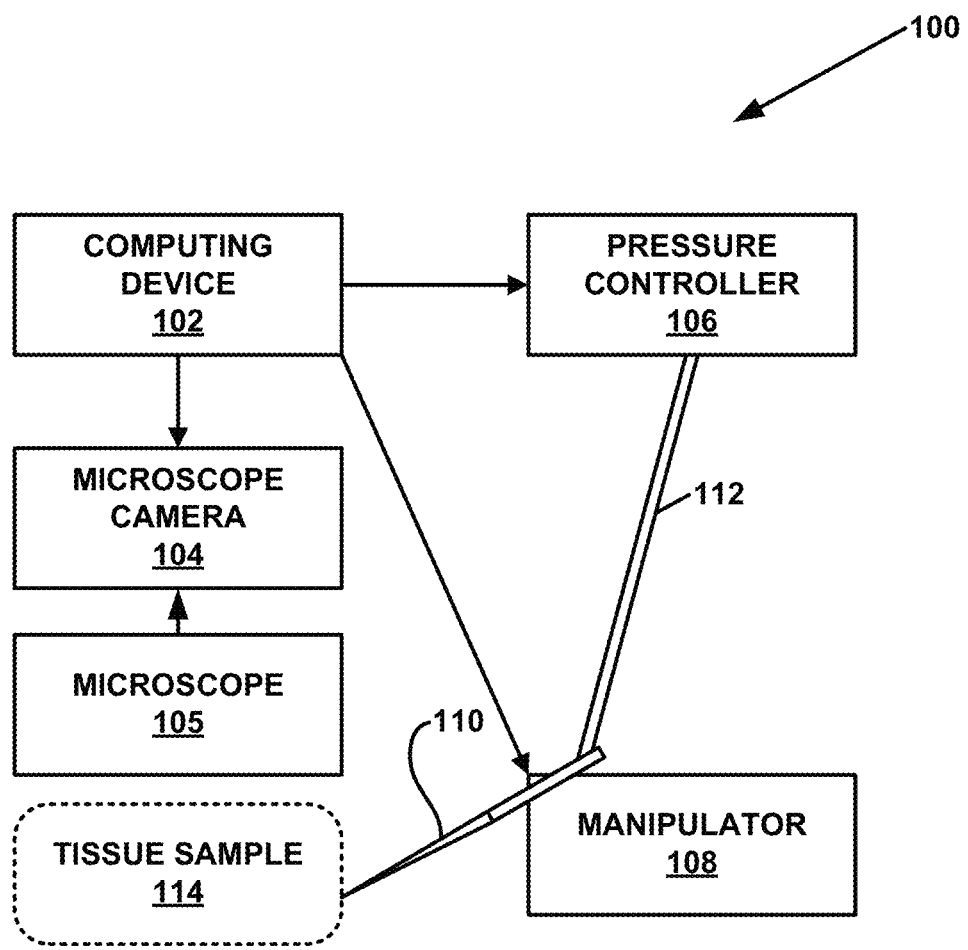
FIG. 1 is a block diagram illustrating an example schematic of an autoinjector that implements techniques of this disclosure.

Manual microinjection enables scientists to inject single cells with molecules or other substances of interest in order to investigate cell decision making, cell differentiation, or other biological processes. However, manual microinjection typically requires extensive training and expertise. Furthermore, manual microinjection typically results in a low number of attempts per sample (e.g., 30-90 attempts per sample) and low yield (e.g., ~15%) for experienced users. Accordingly, the limitations of manual microinjection may restrict the scope of experiments and inhibit broad uptake of the microinjection technology across laboratories.

Other methods of delivery of biological components into cells in tissues include viral delivery and electroporation. Both methods affect large populations of cells but do not allow for single cell specificity. Additionally, both methods are only able to deliver one or two gene products at once with uncontrolled concentrations. Further, electroporation requires particles to be charged for successful delivery.

The current disclosure addresses this issue by describing technical implementations that enable automated injection of controlled solutions into individual cells using, for example, an autoinjector that includes a custom pressure controller, a 3-axis manipulator controlled by user input, and computer-vision feedback. The autoinjector achieves increased yield (e.g., by 44% in one study) with an increased total number of attempts (e.g., 205-1019 in one study) in similar or less amount of time (e.g., 10-45 minutes in one study) as compared to manual injection. The resulting high throughput may enable scientists to screen molecules and genes of interest in tissue to unravel the genetic logic of brain development and evolution, or other biological processes.

Microinjection may circumvent the issues associated with viral delivery and electroporation by allowing for customization of the injection medium and spatial selection of injected cells using a micromanipulator. Thus, the autoinjector of this disclosure may enable single cell resolution with increased yield using a custom open sourced platform that can be readily adapted for broad adaptation across laboratories.

Prior microinjection systems relied on the cells being isolated from the tissues from which the cells originated. In such systems, it may be impossible or difficult to determine how the individual cells behave when the cells are in their host tissues. In vitro systems enable investigation of genetic influence with single cell resolution in controlled environments, which may allow for direct observation of stem cell differentiation and proliferation using optical methods. However, a potential drawback of in vitro systems is the lack of chemical and mechanical cues found in vivo which play significant roles in cell fate determination. Dye-labeling and electroporation may allow for in vivo tracking of progenitor stem cells. However, potential drawbacks may include lack of concentration modulation of gene products, and lack of combination of gene products.

To address these challenges, previous work developed a microinjection protocol for injecting gene products into a developing telencephalon. This work demonstrated the ability to deliver multiple gene products, dye, and CRISPR/Cas9 delivery systems into stem cells allowing for the investigation of the role of genes with single cell resolution. However, manual microinjection may be incredibly time consuming, may result in low yield, and may require expertise. These challenges have limited the adoption of microinjection as a tool for investigating cell fate. Robotic systems have recently enabled the automation of difficult laboratory techniques (e.g. the autopatcher system, as described in U.S. Pat. No. 9,668,804) for tasks that require precise micromanipulation and pressure control. Additionally, previous work has combined computer vision to guide these systems to decrease the amount of time taken to complete the process while increasing yield and reproducibility. In other words, manual injection of substances into cells has a low rate of success and the success rate remains relatively low even when a user performs injections with current modes of robotic assistance. Thus, the process of injecting substances into individual cells using manual microinjection systems, including robot-assisted manual microinjection systems and manual microinjection systems with computer vision, may present a potential bottleneck in conducting biological research.

Techniques of this disclosure may address the potential bottleneck of manual microinjection systems. This disclosure describes an automated computer vision guided microinjector robot for the injection of molecules of interest in organotypic slices (e.g., of a developing mouse brain). The use of an autoinjector may result in a significant increase in yield and efficiency as compared with manual operation, may allow for translation of injected messenger ribonucleic acid (mRNA), and may reduce damage to injected cells. The techniques of this disclosure may be generalizable across tissues by injecting different organotypic slice regions, and across model organisms by injecting human, ferret, and brain organoids. The software (e.g., Python-based software, which may be open-sourced) allows for the customization of the automated injection platform for user specific experiments and hardware. Thus, autoinjector 100 may enable the introduction of genetic products into organotypic slices in a controlled, repeatable fashion by optimizing efficiency and yield as compared with manual systems.

As described herein, an autoinjector is a system for injecting one or more substances into an intact tissue sample. An intact tissue may be a tissue removed from an organism and kept alive using controlled culture conditions. In one example, a robotic manipulator apparatus is configured to hold and position a micropipette. Furthermore, a pressure controller is configured for injecting gas through the micropipette to eject a substance out of the micropipette and into a cell of the tissue. In this example, the system includes a microscope camera positioned to observe an injection site. Additionally, a computing device of the system is configured to receive image data from the microscope camera. The image data may comprise data representing a stream of images of the tissue sample. In this example, the computing device may be configured to output a user interface for display. The user interface may include the stream of images of the tissue sample. Additionally, the computing device may receive, via the user interface, an indication of an indication of a trajectory line drawn by a user on the image of the tissue sample. Furthermore, the computing device may control the robotic manipulator apparatus to move a tip of the micropipette along a path defined by the trajectory line. Additionally, the computing device may control the pressure controller to inject a gas into the micropipette to eject the substance out of the micropipette at one or more points along the path defined by the trajectory line.

FIG. 1 is a block diagram illustrating an example schematic of an autoinjector 100 that implements techniques of this disclosure. Autoinjector 100 is an automated microinjection system. In the example of FIG. 1, autoinjector 100 includes a computing device 102, a microscope camera 104, a microscope 105, a pressure controller 106, and a manipulator 108. Manipulator 108 includes a 3-axis micromanipulator that holds a micropipette 110. In some examples, manipulator 108 is a micromanipulator manufactured by Sensapex, Inc of Oulu, Finland. Microscope camera 104 may be manufactured by Hamatsu Photonics of Hamamatsu City, Japan, or AXIOCAM™ camera manufactured by Carl Zeiss AG of Oberkochen, Germany. Computing device 102 may run custom software.

Computing device 102 may be implemented in various ways. For example, computing device 102 may include a personal computer, a laptop computer, a tablet computer, a smartphone, a server computer, or another type of computing device. In some examples, computing device 102 may be located remotely from the other components of autoinjector 100.

Autoinjector 100 is a platform for injecting molecules of interest (dye, mRNA, etc.) into cells in intact tissue using a 3-axis micromanipulator (i.e., manipulator 108), and a custom pressure rig (i.e., pressure controller 106) controlled by user input into computing device 102. In the example of FIG. 1, autoinjector 100 is set up to inject molecules of interest into cell of a tissue sample 114.

In accordance with a technique of this disclosure, computing device 102 outputs a user interface for display. For example, computing device 102 may output a graphical user interface (GUI) or another type of user interface for display. Computing device 102 may receive indications of user input via the user interface. The user interface and/or other controls of autoinjector 100 may enable the user to set a desired pressure. Pressure controller 106 downregulates incoming pressure (e.g., house pressure) to the desired pressure and delivers the pressure to micropipette 110 (e.g., a glass pipette capillary) via a tube 112. As described herein, manipulator 108 (e.g., a micromanipulator and pipette holder) guides micropipette 110 along a user-defined line guided by a feed from microscope camera 104 and injects cells. This disclosure may refer to the user-defined line as a trajectory or trajectory line. The user-defined line may correspond to a surface of an intact tissue of tissue sample 114. As manipulator 108 progresses along the trajectory line, manipulator 108 may perform a user-specified number of injections according to user-specific spacing and depth parameters. Thus, computing device 102 may control manipulator 108 to move a tip of micropipette 110 along a path defined by the trajectory line.

In the example of FIG. 1, computing device 102 interfaces with all the components of autoinjector 100. This includes pressure controller 106, manipulator 108, and microscope camera 104. Computing device 102 may use images from microscope camera 104 to control the position of micropipette 110 using manipulator 108. Autoinjector 100 uses pressure controller 106 to precisely deliver injection pressure to micropipette 110 during microinjection. As noted above, computing device 102 may use images from microscope camera 104 to control the position of micropipette 110 using manipulator 108. That is, computing device 102 may use actively-updated images from microscope camera 104 to determine a current location of micropipette 110 and to control movement of micropipette 110 to move in the correct manner.

The computer vision guided automated microinjection platform of FIG. 1 (i.e., autoinjector 100) may have a wide variety of applications including injection of various tissues in diverse species, nanoscale 3-dimensional (3D) printing, and drug screening. In some examples, a modular design of autoinjector 100 allows for users to choose their own camera and micromanipulators by adjusting the settings in the user interface presented by computing device 102. In other words, a user may choose which cameras and micromanipulators to use in autoinjector 100.

Thus, autoinjector 100 is a robotic manipulator apparatus configured to hold and position micropipette 110. Autoinjector 100 includes a pressure controller 106 configured for injecting gas through micropipette 110 to eject a substance out of the pipette and into a cell of tissue sample 114. Additionally, autoinjector 100 includes microscope camera 104 positioned to observe an injection site at which micropipette 110 injects the substances into the cell. Microscope camera 104 may generate image data based on light focused on an image sensor of microscope camera 104 by microscope 105. Autoinjector 100 also includes a computing device 102 configured to receive image data from microscope camera 104 and control pressure controller 106 and manipulator 108. The image data may include an image of tissue sample 114. Computing device 102 may output a user interface for display. The user interface may include the image of the tissue sample. Additionally, computing device 102 may receive, via the user interface, an indication of user input of a trajectory of micropipette 110. For instance, computing device 102 may receive an indication of a trajectory line drawn on the image of the tissue sample. Computing device 102 may control manipulator 108 to move a tip of micropipette 110 along the trajectory line, or more specifically, a path defined by the trajectory line. As part of moving the tip of micropipette 110 along the path defined by the trajectory line, computing device 102 may control manipulator 108 to perform injections at specific user-defined spacing intervals and at user-defined injection depths. A user may specify the spacing intervals and injection depths in a user interface that is output for display by computing device 102. Because manipulator 108 is able to perform the injections at consistent injection depths, autoinjector 100 may be able to consistently inject cells occurring at particular depths within tissue sample 114 in a manner that may be challenging for a human user.

Figure 2:
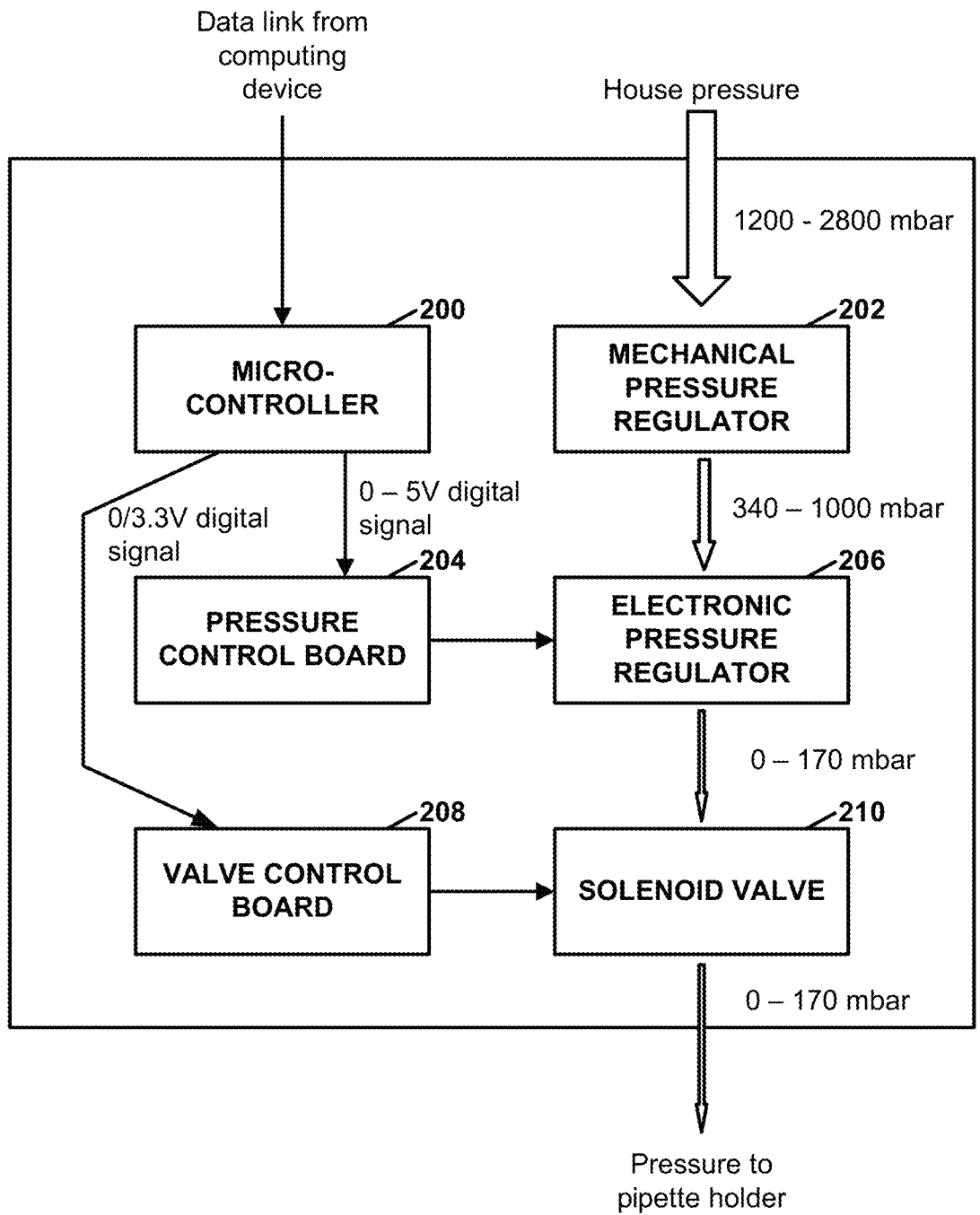
FIG. 2 is a block diagram illustrating example components of a pressure controller in accordance with one or more techniques of this disclosure.

FIG. 2 is a block diagram illustrating example components of pressure controller 106 in accordance with one or more techniques of this disclosure. In the example of FIG. 2, pressure controller 106 includes a microcontroller 200, a mechanical pressure regulator 202, a pressure control board 204, an electronic pressure regulator 206, a valve control board 208, and a solenoid valve 210. In some examples, each of microcontroller 200, pressure control board 204, and valve control board 208 may be implemented using separate electronic circuit boards. In some examples, microcontroller 200 includes an ARDUINO DUE™ microcontroller or an ARDUINO UNO™ microcontroller. In some examples, one or more of microcontroller 200, pressure control board 204, and valve control board 208 may be implemented using the same circuit board.

Mechanical pressure regulator 202 coarsely downregulates house pressure (e.g., 1200-2800 millibar (mbar)) to a first lower pressure (e.g., 340-1000 mbar). Furthermore, in the example of FIG. 2, electronic pressure regulator 206 may perform fine downregulation (e.g., to 0-170 mbar). Microcontroller 200 may control pressure control board 204, which may control electronic pressure regulator 206. Thus, electronic pressure regulator 206 may be controlled by pressure control board 204 and microcontroller 200. When opened, solenoid valve 210 delivers pressure to micropipette 110 (FIG. 1). The pressure triggered using solenoid valve 210 (which is controlled by valve control board 208 and microcontroller 200) is sent to micropipette 110 (e.g., a glass micropipette) for injection. In some examples, micropipette 110 is attached to manipulator 108 at a 45-degree angle on a three-axis manipulator. As mentioned above, manipulator 108 controls the trajectory of micropipette 110 and computing device 102 guides micropipette 110 using microscope feedback. An example algorithm is described in detail in FIG. 12. In the example of FIG. 2, narrow arrows indicate digital interface routes, broader arrows indicate pneumatic routes.

Figure 3:
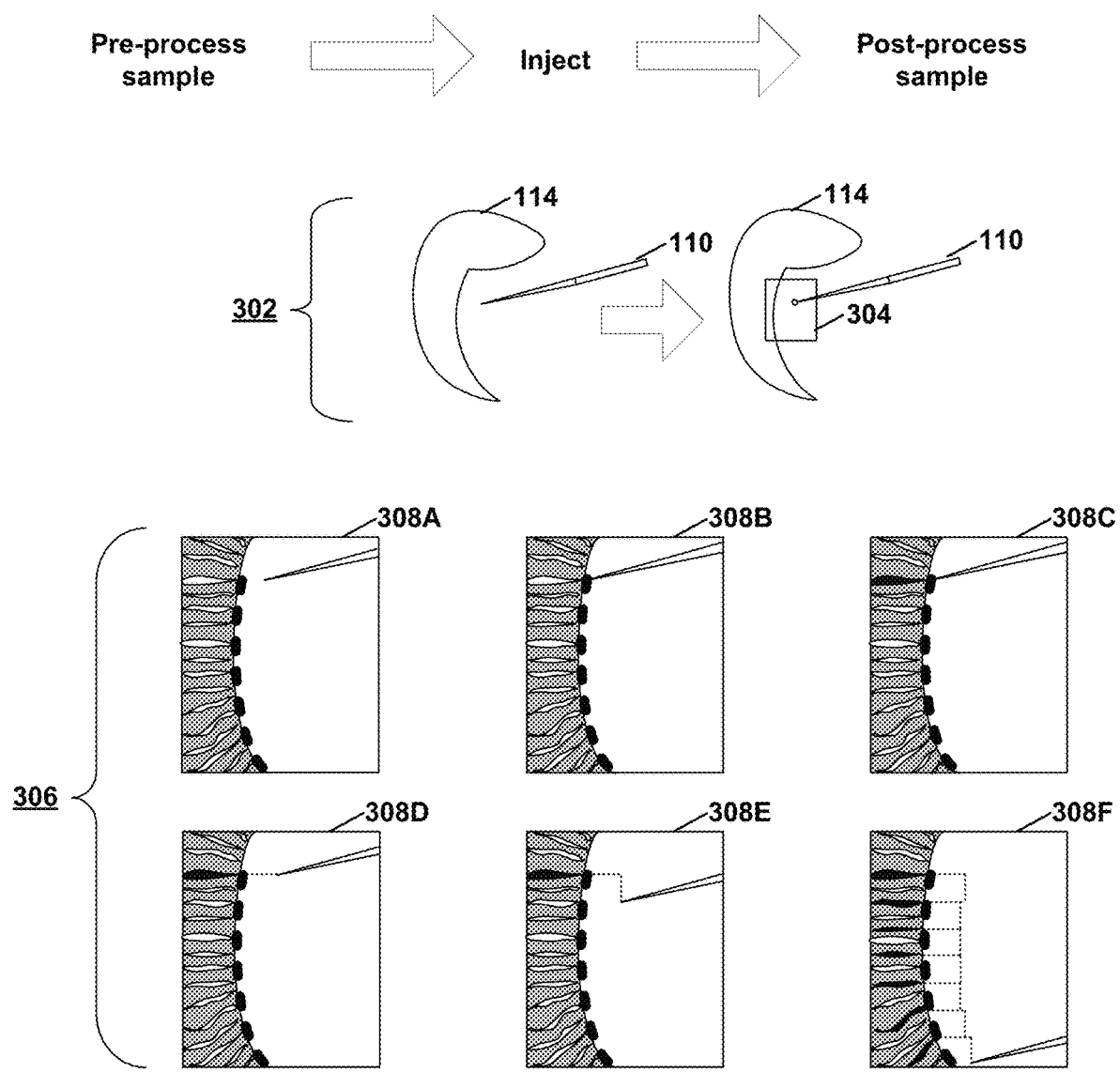
FIG. 3 shows an example general flow of use of the autoinjector in accordance with one or more techniques of this disclosure.

FIG. 3 shows an example general flow of use of autoinjector 100 in accordance with one or more techniques of this disclosure. In the example of FIG. 3, the use of autoinjector 100 is broken down into three phases: a pre-processing phase, an injection phase, and a post-processing phase. In the pre-processing phase, a user or machine may preprocess tissue sample 114. For example, tissue sample 114 may be preprocessed by placing a solution (e.g., a saline solution) and tissue sample 114 in an appropriate sample holder. Furthermore, in the preprocessing phase, the sample holder may be positioned (e.g., by the user or a machine) at an appropriate position to be viewed by microscope 105.

In one example of preprocessing tissue sample 114, tissue sample 114 may be a mouse telencephalon that was dissected and embedded in agarose gel during the preprocessing phase. The mouse telencephalon was then sectioned into 400 micron thick coronal sections using a vibratome (Leica). Glass capillaries (outer diameter 1.8 mm) were pulled into micropipettes using a pipette puller (e.g., using a pipette puller manufactured by Sutter Instruments of Novato, California). In this example, an injection medium was prepared with fluorescent dye dextran coupled to Alexa 488, inserted into pipettes, and loaded onto a pipette holder (e.g., manipulator 108). The tissue slice was loaded into a $CO_2$ independent microinjection medium (CIMM) and positioned on a stage of microscope 105. Micropipette 110 was brought into the field of view of microscope 105 (and hence microscope camera 104) close to the edge of the tissue under 10× magnification with a 10× objective lens and then switched to 20× magnification. To verify micropipette 110 was not clogged, pressure was applied through the GUI and fluorescence was observed. If no fluorescence was observed pipettes were changed and the positioning was repeated.

After preprocessing tissue sample 114, the injection phase may begin. During the injection phase, micropipette 110 is brought into view of microscope camera 104 close to tissue sample 114. The user may then calibrate autoinjector 100 (e.g., in accordance with the examples of FIG. 6A, FIG. 6B, FIG. 7, FIG. 8, FIG. 11) and may draw a desired trajectory line in a GUI. After receiving input of trajectory parameters, the user may set the pressure and initiate autoinjector 100 in the GUI.

Part 302 of FIG. 3 illustrates micropipette 110 in proximity to tissue sample 114. A box 304 indicates an area shown in enhanced detail in part 306 of FIG. 3. Part 306 of FIG. 3 includes images 308A, 308B, 308C, 308D, 308E, and 308F (collectively, "images 308") at occur in sequential order. In images 308, the thick dashed line corresponds a trajectory line drawn by the user along a surface of tissue sample 114. As shown in image 308A, a tip of micropipette 110 is positioned near a top end of the trajectory line. During the injection phase, manipulator 108 moves micropipette 110 to the edge of the tissue (as shown in image 308B), enters a depth into the tissue (as shown in image 308C), pulls out (as shown in image 308D), steps along trajectory to a next point (as shown in image 308E), and continues injection (as shown in image 308F). In images 308, the thin dashed line corresponds to a path defined by the trajectory line drawn by the user. Furthermore, in images 308, injected cells are shown with dark interiors.

During the post-processing phase, a user may observe the behavior of cells in tissue sample 114. In some examples, the user uses microscope camera 104 to make such observations. In other examples, the user may use other instruments to make such observations. The cellular behaviors such as cell division, cell proliferation, the generation of neurons, and other behaviors may be studied in the injected cells of tissue sample 114.

Figure 4A:
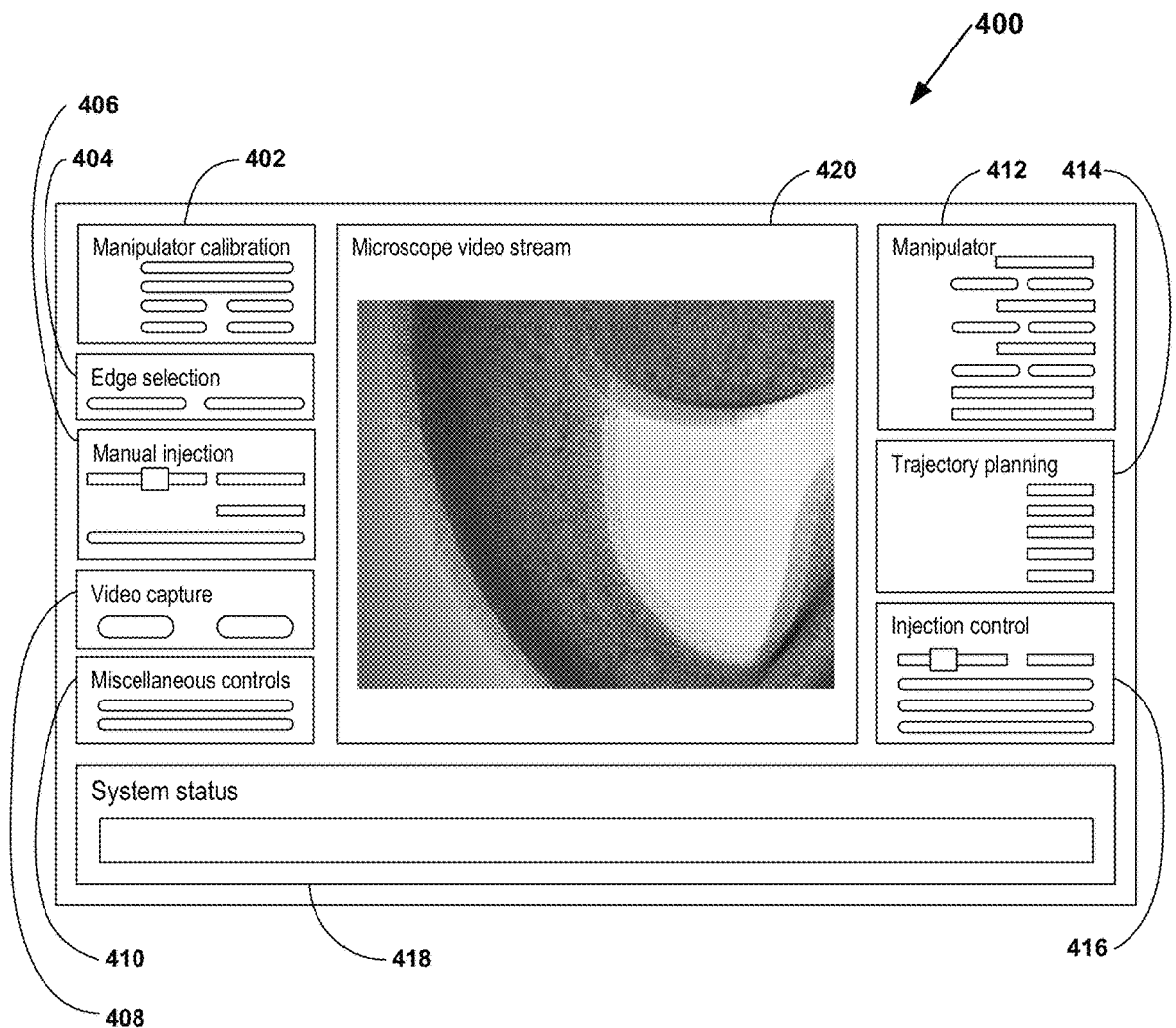
FIG. 4A illustrates an example graphical user interface (GUI) for operating the autoinjector in accordance with one or more techniques of this disclosure.

FIG. 4A illustrates an example graphical user interface (GUI) 400 for operating autoinjector 100 (FIG. 1) in accordance with one or more techniques of this disclosure. Computing device 102 (FIG. 1) may output GUI 400 for display. GUI 400 may be developed in Python or another programming language.

A user may use GUI 400 to control hardware of autoinjector 100. For instance, a user may use GUI 400 to control pressure and to control a trajectory of injection. To do so, the user may first use GUI 400 to set the magnification of microscope 105, followed by calibration, parameter input, and feature selection. Calibration may involve mapping camera axes (i.e., the horizontal and vertical axes of images captured by microscope camera 104) to the manipulator axes (i.e., axes of motion of manipulator 108). In some examples, micropipette 110 may be calibrated in less than 1 minute using two steps.

For example, a user may use GUI 400 to control calibration settings, feature selection, video recording, manipulator location, and trajectory/injection controls. Computing device 102 may use parameters that the user provided as input into GUI 400 to control the trajectory of micropipette 110. The parameters input into GUI 400 may include a number of cells, spacing between injections, depth into tissue, pressure, speed, and distance to pull out of tissue before the next step along the selected trajectory. The number of cells parameter indicates how many cells of tissue sample 114 (FIG. 1) are to be injected. The spacing parameter indicates a distance along the trajectory line between injections. The depth parameter may indicate a depth that micropipette 110 is to penetrate past the trajectory line to perform injection. The pressure parameter indicates a pressure provided into micropipette 110 by pressure controller 106 during an injection. The speed parameter indicates a speed at which manipulator 108 moves micropipette 110. The distance to pull out parameter may indicate a distance in a direction opposite the trajectory line from tissue sample 114 manipulator 108 moves micropipette 110 after an injection. Manipulator 108 may move micropipette 110 along a line generally parallel to the trajectory line at the distance specified by the distance-to-pull-out parameter until the tip of micropipette has traveled the distance specified by the spacing parameter, at which point manipulator 108 may move micropipette 110 toward tissue sample 114 until micropipette is the distance specified by the depth parameter past the trajectory line. Autoinjector 100 may repeat this process for the number of times indicated by the number of cells parameter.

In the example of FIG. 4A, GUI 400 includes calibration controls 402, edge selection controls 404, manual injection controls 406, video capture controls 408, show/hide shapes controls 410, manipulator controls 412, trajectory planning controls 414, injection controls 416, a response monitor 418 and a camera view area 420. Calibration controls 402 may allow the user to calibrate the manipulator X and Y camera frames to those of microscope camera 104 (FIG. 1). Further discussion of calibration is found elsewhere in this disclosure.

Figure 4B:
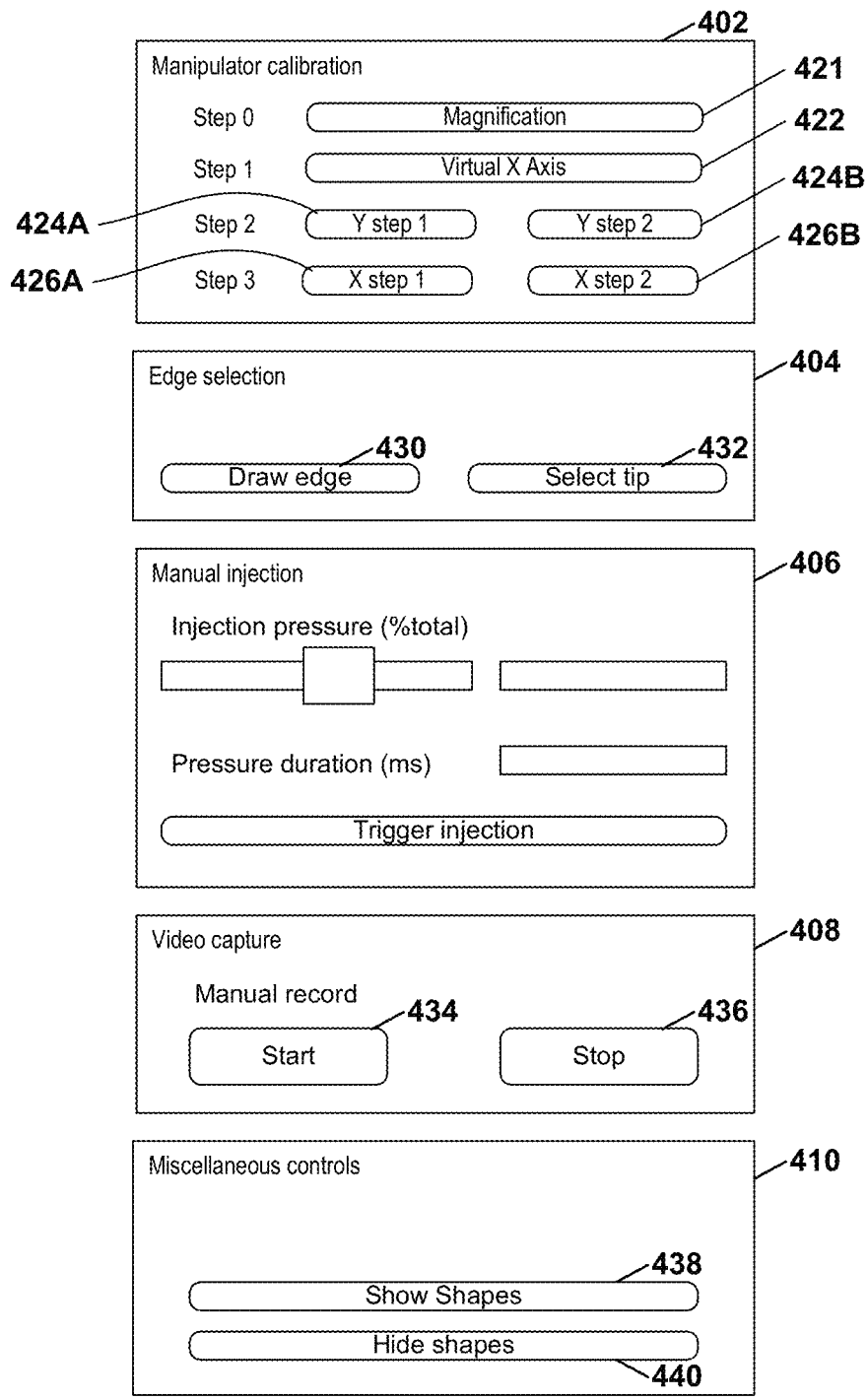
FIG. 4B illustrates example details of the GUI of FIG. 4A in accordance with an aspect of this disclosure.

FIG. 4B illustrates example details of GUI 400 in accordance with an aspect of this disclosure. As shown in FIG. 4B, calibration controls 402 may include a magnification button 421, a virtual x-axis button 422, Y step buttons 424 (including a Y step 1 button 424A and a Y step 2 button 424B), and X step buttons 426 (including an X step 1 button 426A and an X step 2 button 426B). Furthermore, edge selection controls 404 include a "draw edge" button 430 that allows the user to draw a desired trajectory. Edge selection controls 404 also include a select tip button 432. The user may select the select tip button 432 to indicate to computing device 102 to enter a mode in which the user is able to indicate a location of a tip of micropipette 110.

In the example of FIG. 4B, video capture controls 408 include a "Start" button 434 and a "Stop" button 436. Computing device 102 (FIG. 1) may output a pop-up screen in response to receiving an indication of user input to select the "Start" button 434. The pop-up screen may include controls that enable the user to select how video capture of an injection process is performed. For instance, in one example, the pop-up window includes a control (e.g., a dropdown menu, radio boxes, etc.) that allows the user to select a codec (e.g., "Intel Codec") for recording the video. When the user presses the "Stop" button 436, computing device 102 may show the name of a video file in response monitor 418 and computing device 102 may save the video file in a folder (e.g., a filter on the desktop>>Autoinjector_Code>>Video Data>>Date>>time, where data is the date and time is the time the video was started). The video file includes data representing the captured video.

Show/hide shapes controls 410 include controls that enable the user to display or hide the user-drawn trajectory in the video feed shown in camera view area 420. For instance, in the example of FIG. 4B, show/hide shapes controls 410 include a show shape button 438 and a hide shapes button 440.

Response monitor 418 may provide updates to the user with feedback from the interface and may report useful information such as parameter change updates, video output files, number of attempts of injection, and so on.

Figure 4C:
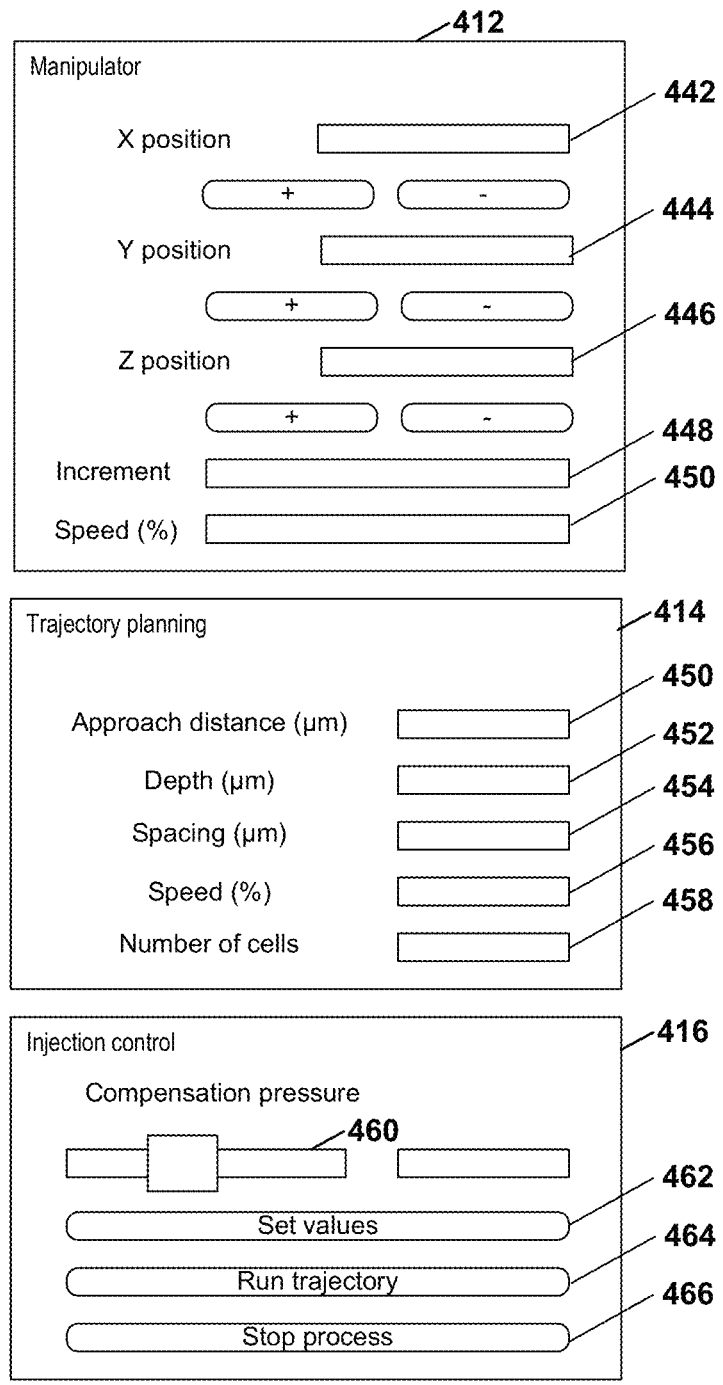
FIG. 4C illustrates example details of the GUI of FIG. 4A in accordance with an aspect of this disclosure.

FIG. 4C illustrates example details of GUI 400 in accordance with an aspect of this disclosure. As shown in the example of FIG. 4C, manipulator controls 412 may display the positions of manipulator 108. For instance, box 442 may indicate an x-axis position of micropipette 110, box 444 may indicate a y-axis position of micropipette 110, and box 446 may indicate a z-axis position of micropipette 110. The plus (+) and minus (−) buttons below box 442, box 444, and box 446 allow the user to use GUI 400 to advance micropipette 110 (FIG. 1) along x, y, and z axes of motion of manipulator 108, respectively. Furthermore, in the example of FIG. 4C, manipulator controls 412 include an increment feature 448 and a speed feature 449. Increment feature 448 may display and allow the user to update a distance that manipulator 108 increments or decrements the position of micropipette 110 in response to receiving indications of user input selecting the plus or minus buttons. Speed feature 449 may display and allow the user to update a speed at which manipulator 108 moves micropipette 110 in response to receiving indications of user input selecting the plus or minus buttons. For instance, the user may see the increment (in microns) and speed (in % total, 100% is fine in most cases) by typing the values into GUI 400, and/or by pressing the "+" or "−". buttons.

In the example of FIG. 4C, trajectory planning controls 414 include the following controls:
  Approach distance control 450—the distance the pipette pulls out of the tissue before advancing to next injection site in microns.
  Depth control 452—the depth into the tissue the pipette goes upon injection, in microns.
  Spacing control 454—the spacing between subsequent injections in microns.
  Speed control 456—the speed of manipulator 108 in % total
  Number of Cells control 458—the number of injection attempts, which in some examples may be arbitrary large as trajectory will stop when end of line is reached see section V for more details).

Furthermore, in the example of FIG. 4C, injection controls 416 include a compensation pressure slider 460 that enables the user to control the percentage of total pressure let through electronic pressure regulator 206 (FIG. 2). Additionally, injection controls 416 includes a "set values" button 462, a "run trajectory" button 464, and a "stop process" button 466. Computing device 102 may lock in the parameter values set in trajectory planning controls 414 in response to receiving an indication of user input indicating selection of the "set values" button 462. Computing device 102 may cause manipulator 108 and pressure controller 106 to run an injection process based on a trajectory. Computing device 102 may stop the injection process in response to receiving an indication of user input to select "stop process" button 466.

Figure 5A:
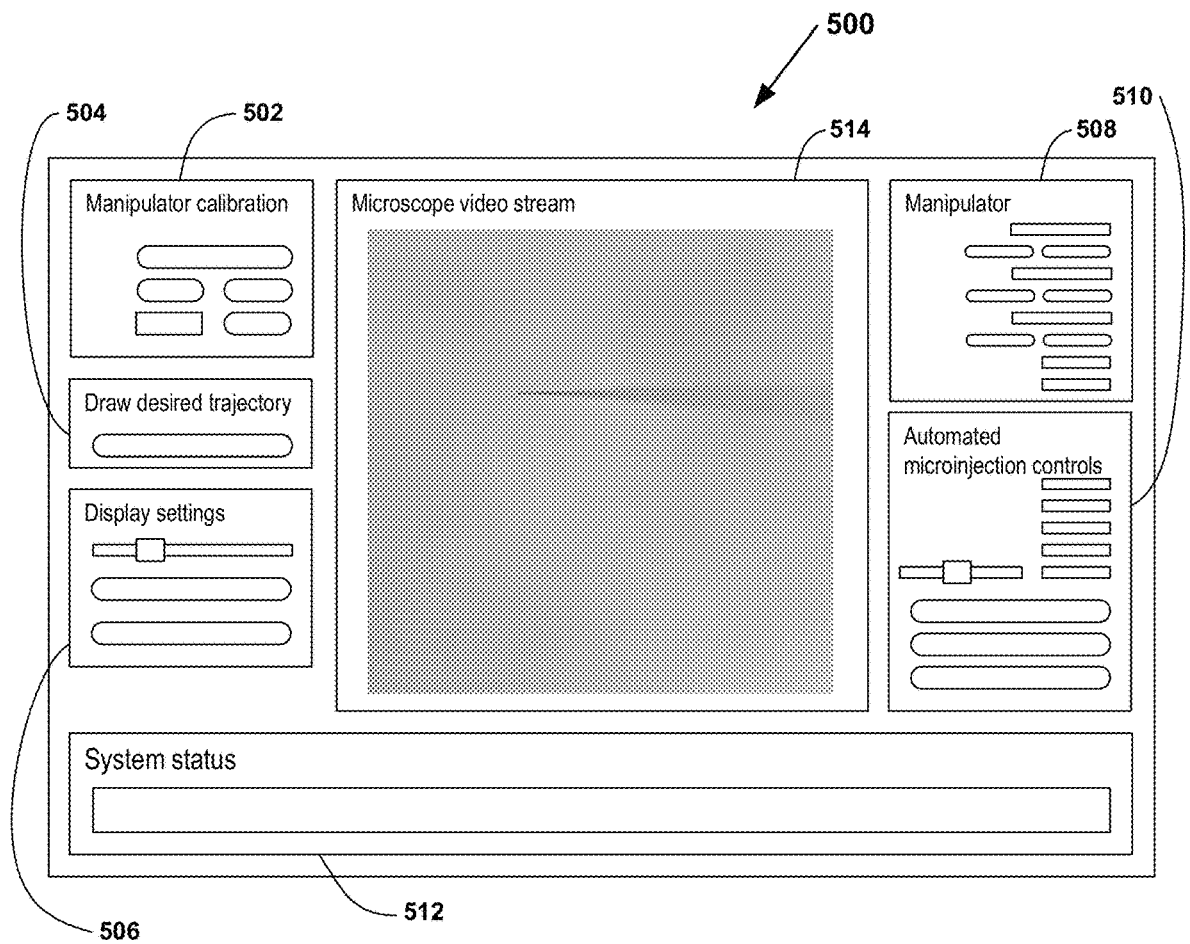
FIG. 5A shows an example alternative GUI in accordance with a technique of this disclosure.
Figure 5B:
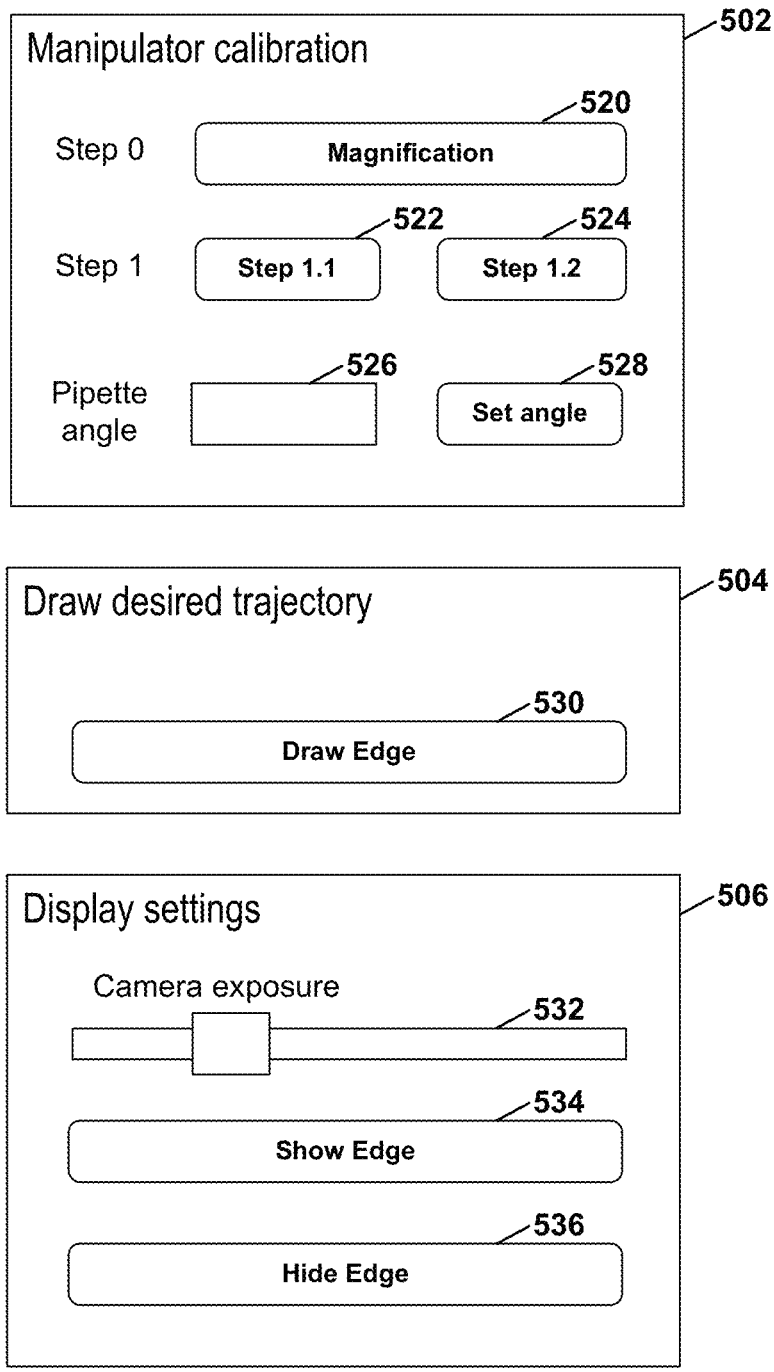
FIG. 5B illustrates example details of the GUI of FIG. 5A.
Figure 5C:
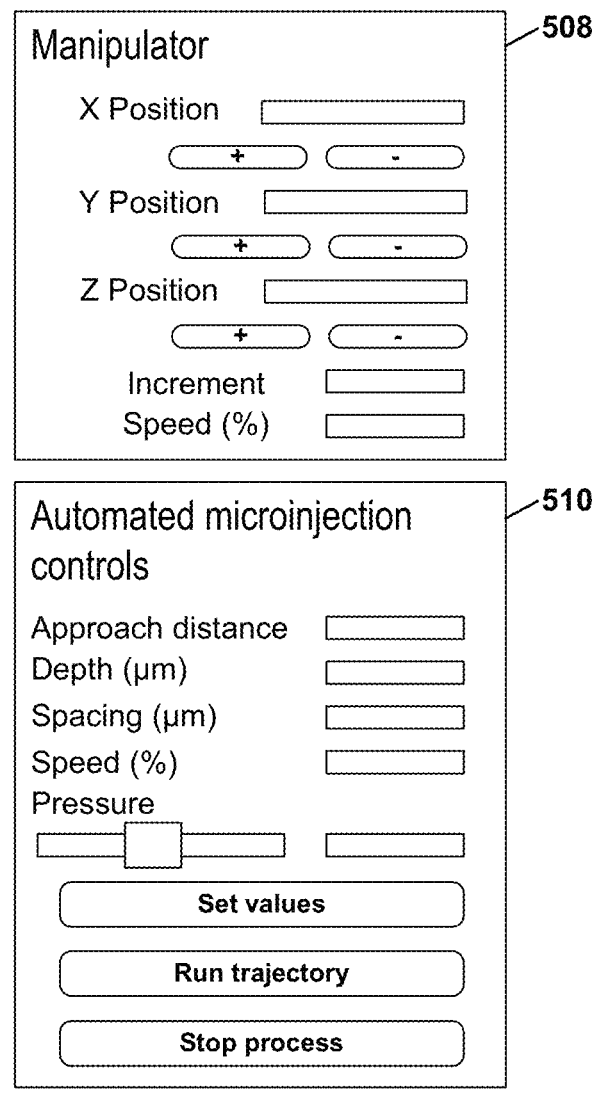
FIG. 5C illustrates example details of the GUI of FIG. 5A.

FIG. 5A shows an example alternative GUI 500 in accordance with a technique of this disclosure. A user may use GUI 500 in a similar fashion to GUI 400 of FIG. 4A. In the example of FIG. 5A, GUI 500 includes manipulator calibration controls 502, a trajectory drawing control 504, display settings controls 506, manipulator controls 508, automated microinjection controls 510, and response monitor 512. Additionally, GUI 500 includes a microscope video stream area 514 that includes live images from microscope camera 104. Response monitor 512 may function in the same or similar manner as response monitor 418 (FIG. 4A). FIG. 5B illustrates example details of the GUI of FIG. 5A. Specifically, FIG. 5B shows manipulator calibration controls 502, trajectory drawing control 504, and display settings controls 506 in greater detail. FIG. 5C illustrates example details of the GUI of FIG. 5A. Specifically, FIG. 5C shows manipulator controls 508 and automated microinjection controls 510 in greater detail.

In FIG. 5B, manipulator calibration controls 502 allow the user to calibrate manipulator axes and the camera axes. Manipulator calibration controls 502 includes a magnification button 520, a step 1.1 button 522, a step 1.2 button 524, a pipette angle box 526, and a set angle button 528. Computing device 102 may change a magnification level of microscope camera 104 in response to receiving an indication of user input selecting magnification button 520. Computing device 102 may cause manipulator 108 to advance micropipette 110 in the manipulator y-axis in response to receiving an indication of user input to step 1.1 button 522. Computing device 102 may complete the calibration process after receiving an indication of user input to select the tip of micropipette 110 after manipulator 108 has advanced the tip of micropipette 110 and after computing device 102 has received an indication of user input to select the step 1.2 button 524. Computing device 102 may receive an indication of user input in pipette angle box 526 specifying an angle at which manipulator 108 holds micropipette 110. Computing device 102 may set the angle indicated in pipette angle box 526 when computing device 102 receives an indication of user input selecting the set angle button 528.

Furthermore, in the example of FIG. 5B, computing device 102 may output a pop-up user interface showing a current image from microscope camera 104 in response to receiving an indication of user input to select the draw edge button 530. Computing device 102 may receive an indication of a user input of a trajectory line traced by the user in the current image shown in the pop-up interface. In some examples, the user may draw the trajectory line directly in GUI 500 (e.g., in microscope video stream area of GUI 500). Slider 532 in display settings controls 506 may allow a user to adjust an exposure setting of microscope camera 104. Computing device 102 may show a trajectory line in microscope video stream area 514 in response to receiving an indication of user input selecting show edge button 534. Computing device 102 may hide the trajectory line in microscope video stream area 514 in response to receiving an indication of user input selecting hide edge button 536.

In FIG. 5C, manipulator controls 508 include the same buttons, which have the same functions, as manipulator controls 412 of FIG. 4C. Furthermore, as shown in the example of FIG. 5C, trajectory planning controls 414 and injection controls 416 of FIG. 5C are merged into automated microinjection controls 510.

Figure 6A:
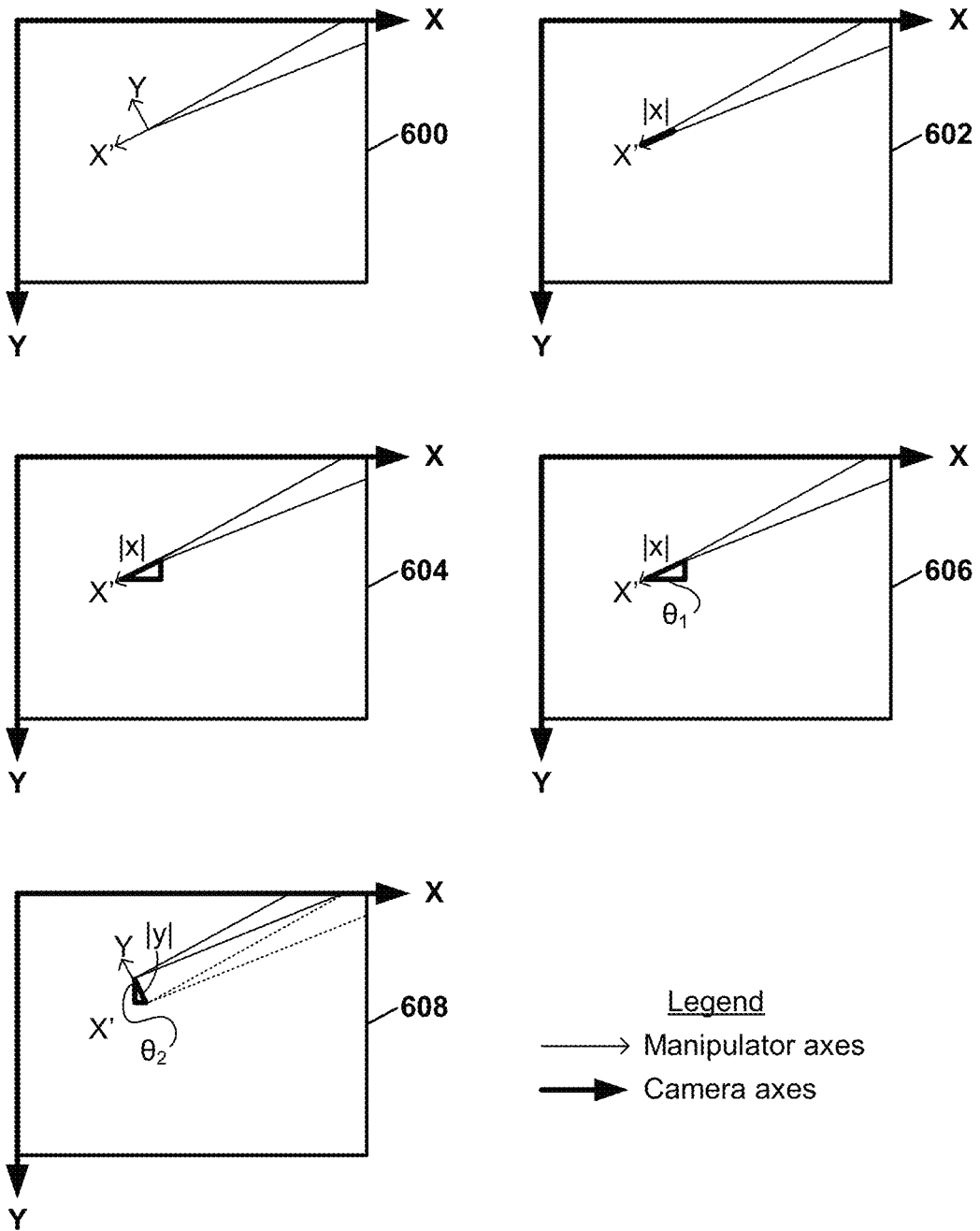
FIG. 6A illustrates an example calibration protocol in accordance with one or more techniques of this disclosure.

FIG. 6A illustrates an example calibration protocol in accordance with one or more techniques of this disclosure. In some examples, calibration is only required when a pipette is changed. In the example of FIG. 6A, image 600 shows a tip of micropipette 110 and the associated axes. Manipulator axis X' is aligned with a lengthwise direction of micropipette 110 and manipulator axis Y is perpendicular to manipulator axis X'. As shown in image 602, manipulator 108 may advance micropipette 110 during calibration along manipulator axis X' by a distance denoted |x|. The distance that manipulator 108 advances micropipette 110 is indicated in image 602 with a thick black line. Image 604 shows a triangle having a hypotenuse defined by |x|. Image 606 shows an angle $\theta_1$ of a corner of the triangle corresponding to the tip of micropipette 110 after manipulator 108 has advanced micropipette 110. As shown in image 608, this process may be repeated for the manipulator Y dimension to determine an angle $\theta_2$ present at a corner of a triangle having a hypotenuse of length |y| when manipulator 108 moves micropipette 110 in the manipulator Y axis. As described elsewhere in this disclosure, computing device 102 may use the angles $\theta_1$ and $\theta_2$ to compensate for the differences between the manipulator axes and the camera axes.

Figure 6B:
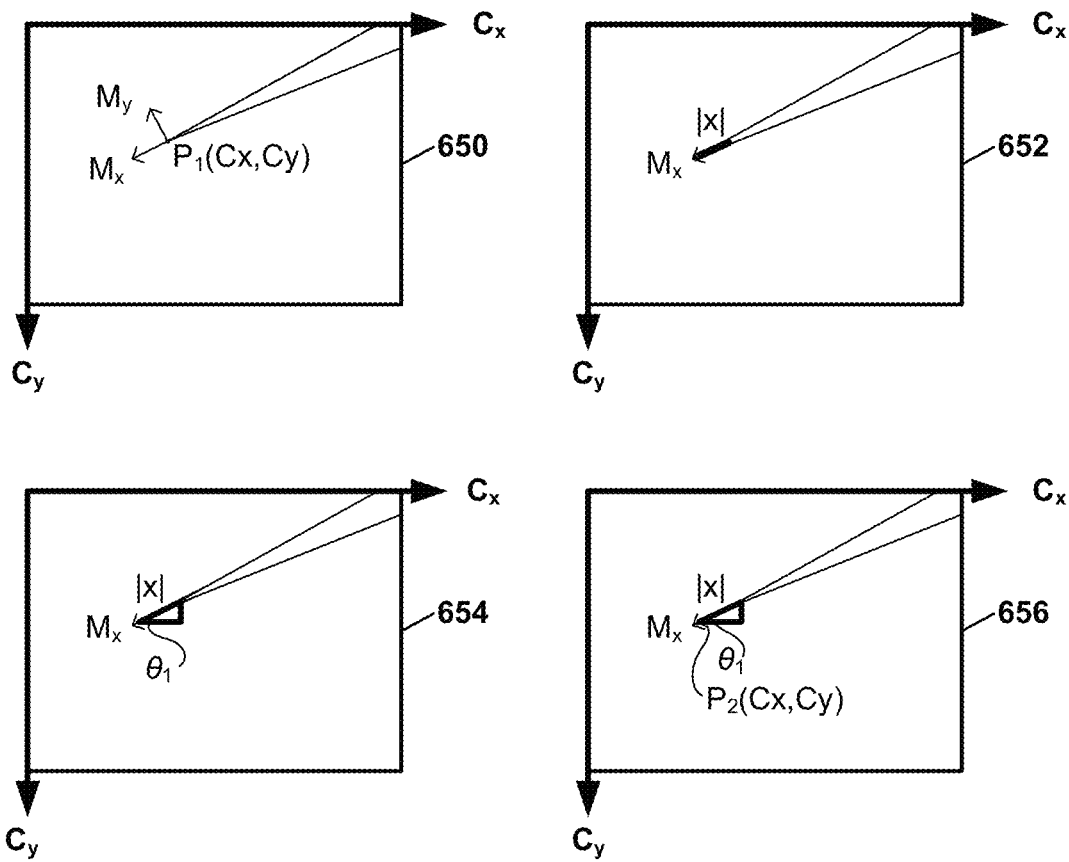
FIG. 6B illustrates an example calibration protocol in accordance with one or more techniques of this disclosure.

FIG. 6B illustrates an example calibration protocol in accordance with one or more techniques of this disclosure. In the example of FIG. 6A, image 650 shows a tip of micropipette 110 and the associated axes. Manipulator axis $M_x$ is aligned with a lengthwise direction of micropipette 110 and manipulator axis $M_y$ is perpendicular to manipulator axis $M_x$. As shown in image 652, manipulator 108 may advance micropipette 110 during calibration along manipulator axis $M_x$ by a distance denoted |x|. The distance that manipulator 108 advances micropipette 110 is indicated in image 652 with a thick black line. Image 654 shows a triangle having a hypotenuse defined by |x|. Image 656 shows an angle $\theta_1$ of a corner of the triangle corresponding to the tip of micropipette 110 after manipulator 108 has advanced micropipette 110. In contrast to FIG. 6A, it may be unnecessary to determine the angle $\theta_2$ because, as described below with reference to FIG. 11, determining the angle $\theta_1$ may be sufficient to calibrate the camera axes and the manipulator axes.

Figure 7:
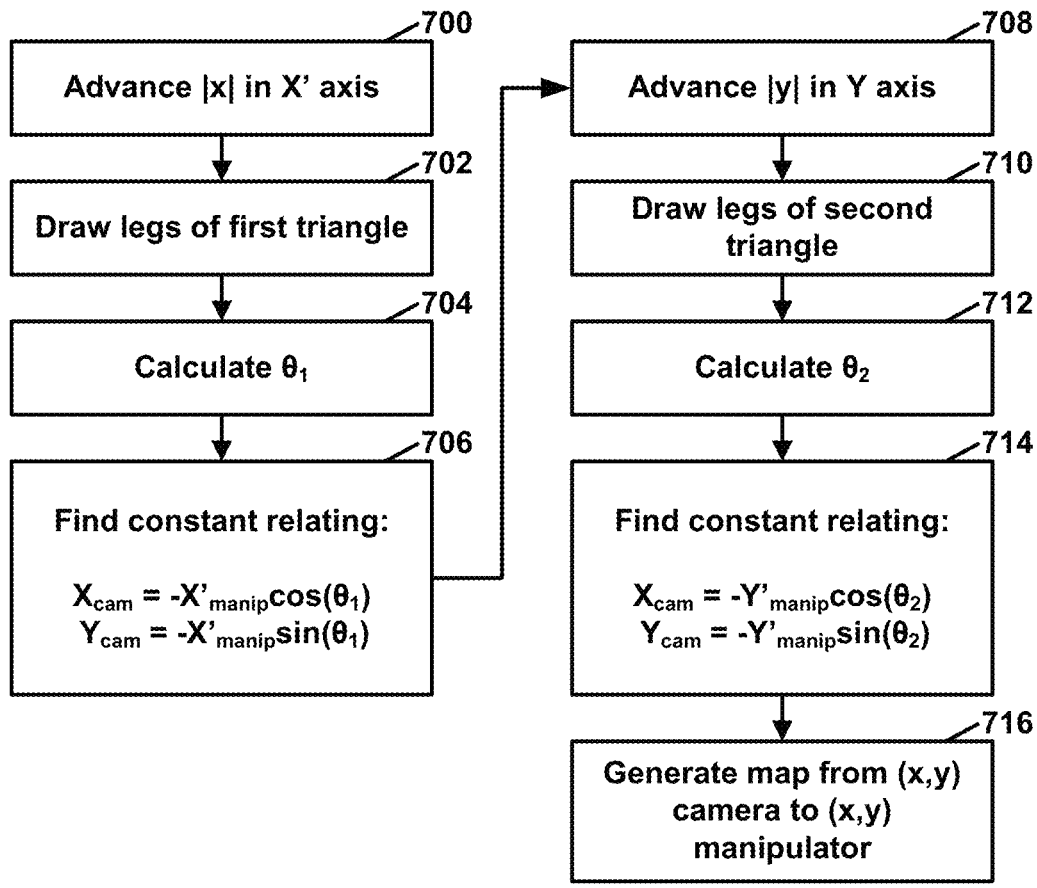
FIG. 7 is a flowchart illustrating an example calibration protocol in accordance with one or more techniques of this disclosure.

FIG. 7 is a flowchart illustrating an example calibration protocol in accordance with one or more techniques of this disclosure. The flowcharts of this disclosure are provided as examples. In other examples, operations may include more, fewer, or different actions. In other examples, steps may be performed in different orders.

In the example of FIG. 7, manipulator 108 may advance the tip of micropipette 110 by a distance of |x| in the manipulator X' axis (i.e., the lengthwise axis of micropipette 110) (700), as shown in image 602 of FIG. 6. Computing device 102 may then draw the legs of a first triangle whose hypotenuse is defined by a position of the tip of micropipette 110 prior to moving the distance of |x| in the manipulator X' axis and a position of the tip of micropipette 110 after moving the distance of |x| in the manipulator X' axis (702), as shown in image 604 of FIG. 6A. Next, computing device 102 may calculate an angle $\theta_1$ as arctan X1/X2, where X1 and X2 are the lengths of the legs of the first triangle (704), as shown in image 606 of FIG. 6A. Computing device 102 may then find a constant relating the camera X axis ($X_{cam}$) and the camera Y axis ($Y_{cam}$) to the manipulator X axis ($X'_{manip}$) and the manipulator Y axis ($Y_{manip}$) as $X_{cam}=-X'_{manip}\cos(\theta_1)$ and $Y_{cam}=-X'_{manip}\sin(\theta_1)$ (706). The constant may be denoted as $R(\theta)$ in equation (5), which is described with reference to FIG. 11, below.

Autoinjector 100 may repeat these steps for Y. That is, manipulator 108 may advance the tip of micropipette 110 by a distance of |y| in the manipulator Y axis (708). Computing device 102 may then draw legs of a second triangle whose hypotenuse is defined by a position of the tip of micropipette 110 prior to moving the distance of |y| in the manipulator Y axis and a position of the tip of micropipette 110 after moving the distance of |y| in the manipulator Y axis (710). Next, computing device 102 may calculate an angle $\theta_2$ as arctan Y1/Y2, where Y1 and Y2 are the lengths of the legs of the second triangle (712). Computing device 102 may then find a constant, $Y_{manip}$, that relates $X_{cam}=-Y_{manip}\cos(\theta_2)$ and $Y_{cam}=-Y_{manip}\sin(\theta_1)$ (714).

Computing device 102 may then create a map from the camera axes to the manipulator axes (716). For instance, computing device 102 may create the map as:

$$X_{cam}=-X'_{manip}\cos(\theta_1)+Y_{manip}\sin(\theta_2)$$

$$Y_{cam}=-X'_{manip}\sin(\theta_1)+Y_{manip}\cos(\theta_2)$$

Subsequently, computing device 102 may use this map to translate points in the trajectory line drawn by the user into coordinates defined in terms of manipulator axes. In some examples, it may be unnecessary to calibrate both X and Y. Thus, in some examples, actions (700) through (706) may be omitted or actions (708) through (714) may be omitted.

Figure 8:
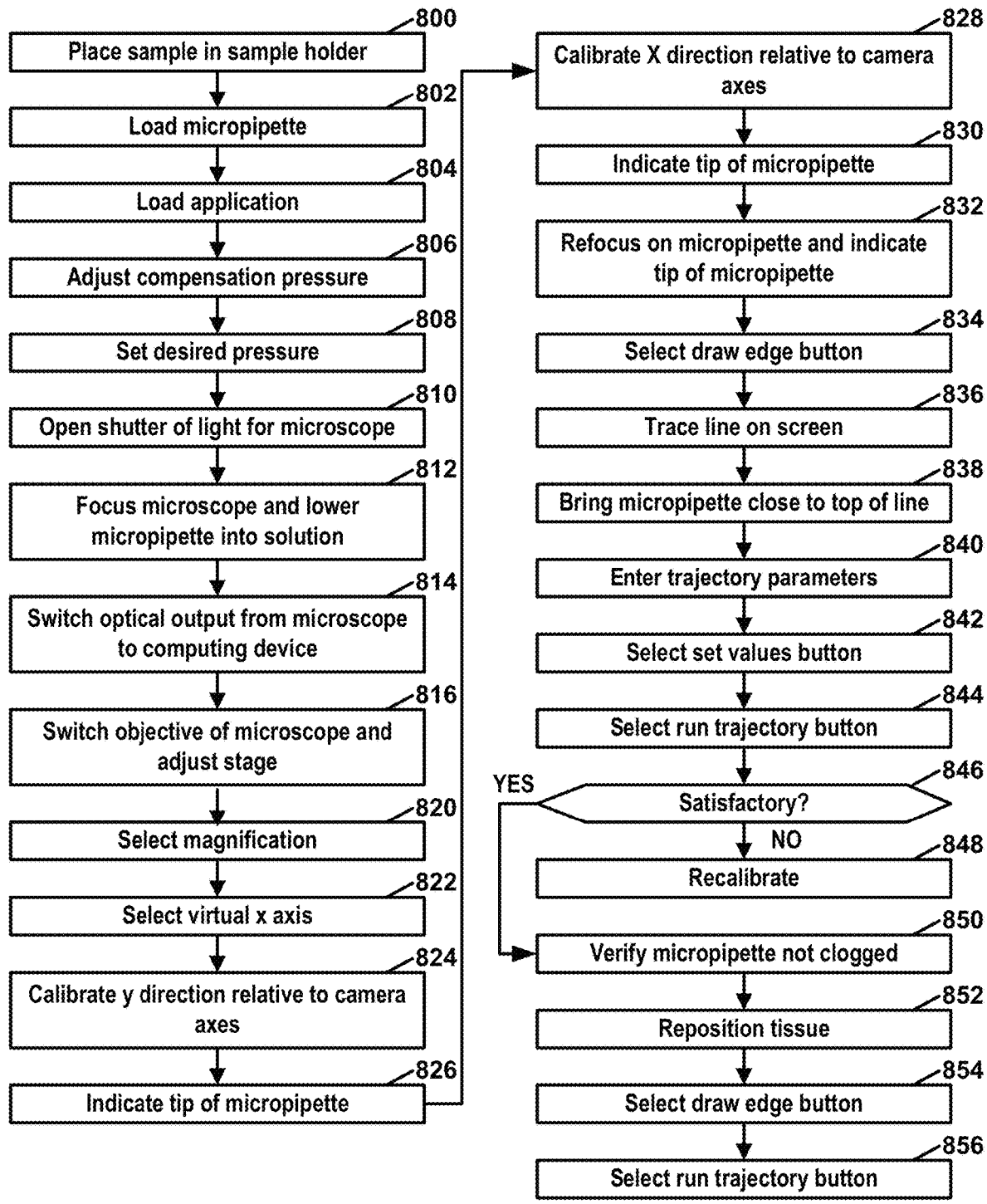
FIG. 8 is a flowchart illustrating an example series of steps that a user may perform to use the autoinjector in accordance with one or more techniques of this disclosure.

FIG. 8 is a flowchart illustrating an example series of steps that a user may perform to use autoinjector 100 in accordance with one or more techniques of this disclosure. In the example of FIG. 8, a user of autoinjector 100 may first place tissue sample 114 in a sample holder on a microscope stage (800). Additionally, the user may load micropipette 110 with an injection medium and may mount micropipette 110 onto manipulator 108 (802). In some examples, the end of manipulator 108 aligns with the end of a sliding stage and is parallel to the axis. The user may also instruct computing device 102 to load an application for controlling autoinjector 100 (804). For instance, the user may instruct computing device 102 to load the application by clicking an "Autoinjector" shortcut on a desktop. The application may cause computing device 102 to output a graphical user interface for display. For instance, the application may cause computing device 102 to output GUI 400 (FIG. 4A) or GUI 500 (FIG. 5A) for display. For ease of explanation, this disclosure refers to GUI 400 when describing the flowchart of FIG. 8.

If manipulator 108 loaded correctly, GUI 400 displays numbers in manipulator controls 412. Before submerging micropipette 110 into the solution that contains tissue sample 114, it may be necessary set a compensation pressure to prevent unwanted clogging. Pressure controller 106 may constantly apply the compensation pressure to micropipette 110 while a tip of micropipette 110 is submerged in the solution. Application of the compensation pressure to micropipette 110 may prevent clogging by counteracting pressure applied by the solution onto the injection substance in micropipette 110. In the absence of the compensation pressure, pressure applied by the solution may sweep matter from the solution into micropipette 110, resulting in micropipette clogging. Accordingly, the user may adjust a compensation pressure (806). In one example, the user may adjust the compensation pressure by sliding a compensation pressure slide 460 (FIG. 4C) to a value and the selecting the "set values" button 462 (FIG. 4C). In some examples, the compensation pressure may be 24%-45% of a pressure provided by mechanical pressure regulator 202 (FIG. 2). For example, if the pressure output by mechanical pressure regulator 202 is 2000 mbar and the compensation pressure is set to 25%, the pressure output by electronic pressure regulator 206 (FIG. 2) is equal to 500 mbar. This causes pressure controller 106 to apply pressure to micropipette 110.

Furthermore, the user may set a desired pressure (808). In some examples, the user may set the desired pressure by turning a mechanical knob. The units may be in pounds per square inch (1.08 PSI=75 mbar, which is what we use in our experiments for dye, 1.81 PSI=125 mbar for use with mRNA). The pressure may vary widely based on the solution, so the pressure may be more of a relative value and whatever pressure produces appropriate fluorescence is what the user may wish to use.

Continuing the example operation of FIG. 8, the user may also open a shutter of light for microscope 105 (810). For instance, the user may flip a trans-shutter switch to open the shutter of light for microscope 105. Additionally, in the example of FIG. 8, the user may bring a desired area of tissue sample 114 into focus under a 10× objective and lower micropipette 110 into a solution in this area. The user may be able to see that micropipette 110 has been submerged by observing a slight dimple in the water. Before going lower, the user may search the entire Z area for micropipette 110 using the microscope focus. Once the user has found micropipette 110, the user may lower micropipette 110 into the solution in small steps and refocus. The user may repeat this process until micropipette 110 is in the same focal plane as the tissue.

Furthermore, in some examples, the user may switch an optical output of microscope 105 from a microscope eyepiece (i.e., an eyepiece of microscope 105) to microscope camera 104, which provides image data to computing device 102 (814). In some examples, the image may initially appear as all white because the brightness is too high. On microscope 104, the user may adjust the brightness to bring the tissue and micropipette 110 into focus. The user can adjust the speed of manipulator 108 to 4.

The user may also switch the objective of microscope 105 and adjust the position of the stage (816). For instance, the user may switch the objective to 20× and may refocus on micropipette 110 and the tissue. The user may have to adjust the stage to get tissue sample 114 back to a desired location. To move the stage, the user may flip a switch to manual and use a joystick. After moving stage to desired location, the user may flip the switch back to automatic, which may lock the stage in place and may prevent undesired motion of the stage.

The user may then select magnification button 421 (FIG. 4B) in the top left of GUI 400 (820). In response to receiving an indication of selection of magnification button 421, computing device 102 may output a window for display that prompts the user to select a magnification level. For example, the user may select a magnification level (e.g., 20×, 10×, etc.) and press 'Ok'.

Furthermore, the user may select a virtual X axis (822). The virtual X axis is orthogonal to the manipulator Z axis. Typically, the manipulator Z axis is vertical with respect to a surface on which autoinjector 100 rests. In contrast to the virtual X axis, the manipulator X axis is aligned with a lengthwise axis of micropipette 110 when micropipette 110 is held by manipulator 108. To select the virtual X axis, the user may select the virtual x-axis button 422 (FIG. 4B). Selecting virtual X axis button 422 may cause computing device 102 to output a popup window for display. Pressing ok in the popup window may cause the manipulator 108 to advance, the user may then press ok again. In some examples, the step of selecting the virtual X axis is required when the angle of the virtual X axis relative to the manipulator X axis is unknown. However, in some examples, the angle between the virtual X axis and the manipulator X axis is fixed at 45°, so the user does not typically have to do anything beyond clicking Ok in both popup windows and refocusing the tip. In examples where GUI 500 is used, the user may directly enter the angle of micropipette 110 relative to the virtual X axis in pipette angle box 526.

Next, the user may calibrate the Y direction of manipulator 108 (i.e., the manipulator y axis) relative to the camera axes (824). The camera axes may correspond to the width and height axes of an image sensor of microscope camera 104. Calibrating the Y direction of manipulator 108 relative to the camera axes ensures that the Y direction of manipulator 108 is the same as the direction of the height axis of microscope camera 104. Thus, when properly calibrated, micropipette 110 may appear to move vertically in images generated by microscope camera 104 when manipulator 108 moves micropipette 110 in the Y direction.

To calibrate the Y direction of manipulator 108 relative to the camera axes, the user may refocus on the pipette tip and click the tip of micropipette 110 with a cursor. In response to the selection of the tip of micropipette 110, computing device 102 may cause a visual indicator (e.g., a white dot or other form of visible marker) to appear in camera view area 420 where the user clicked. The user may then press the Y step 1 button 424A as shown in FIG. 4B and press OK in the popup window. In response, manipulator 108 may automatically move micropipette 110 a predetermined distance in the Y direction of manipulator 108. The user may then click on the tip of the pipette again and press Y step 2 button 424B as shown in FIG. 4B (826). The Y direction of manipulator 108 may now be calibrated.

Because the Y direction of manipulator 108 might not initially be aligned with the vertical axis of microscope camera 104, the images generated by microscope camera 104 may show that the tip of micropipette 110 has moved horizontally as manipulator 108 moves micropipette 110 in the Y direction. By clicking the tip of micropipette 110 twice in the manner described above, computing device 102 may determine an X direction offset that corresponds to how much the tip of micropipette 110 has moved horizontally in the images for a predetermined amount of movement of micropipette 110 in the Y direction of manipulator 108. In other examples, rather than relying on the user to click the tip of micropipette 110, computing device 102 may execute image processing software that automatically recognizes the position of the tip of micropipette 110 before and after manipulator 108 moves micropipette 110 in the Y axis of manipulator 108. From the X direction offset and the predetermined amount of movement of micropipette 110 in the Y direction of manipulator 108, computing device 102 may use basic trigonometric principles to determine a Y offset angle that corresponds to an angle between the vertical axis of microscope camera 104 and the Y direction of manipulator 108. In some examples, computing device 102 may rotate images produced by microscope camera 104 by the Y offset angle such that movements of micropipette 110 in the Y direction of manipulator 108 appear to be vertical movements in the 2-dimensional images that computing device 102 shows in camera view area 420.

Additionally, the user may repeat this process for the X direction of manipulator 108. That is, the user may calibrate the X direction of manipulator 108 relative to the camera axes (828). Calibrating the X direction of manipulator 108 relative to the camera axes may ensure that the X direction of manipulator 108 is the same as the direction of the width axis of microscope camera 104. Thus, when properly calibrated, micropipette 110 may appear to move horizontally in images generated by microscope camera 104 when manipulator 108 moves micropipette 110 in the X direction.

To calibrate the X direction relative to the camera axes, the user may select the tip of micropipette 110 with a cursor and then press the X step 1 button 426A as shown in FIG. 4B (830). Manipulator 108 may then advance micropipette 110 a predetermined distance in the X direction of manipulator 108. In other words, manipulator 108 may move micropipette 110 along the manipulator X axis. Because the manipulator X axis is aligned with the lengthwise axis of micropipette 110 and micropipette 110 is mounted on manipulator 108 with an angle (e.g., 45°) relative to the virtual X axis (e.g., an axis horizontal relative to a plane on which autoinjector 100 rests), moving micropipette 110 along the manipulator X axis may move the tip of micropipette 110 further from or nearer to a lens of microscope 105. Because the tip of micropipette 110 moves further from or nearer to the lens of microscope 105, the tip of micropipette 110 may move out of focus. The user may then refocus on micropipette 110 and select the tip of micropipette 110 (832). The user may then select X step 2 button 426B as shown in FIG. 4B. Both axes are now calibrated.

In some examples, such as examples where GUI 500 is used, the user may skip calibration of the X direction of manipulator 108 relative to the camera axes. That is, in such examples, actions (822), (828), (830), and (832) may be skipped. In such examples, the x-axis of micropipette 110 is the lengthwise axis of micropipette 110 and the true x axis (i.e., the virtual X axis) may correspond to a horizontal direction relative to a surface on which autoinjector 100 rests. In examples where the user skips calibration of the X direction, the user may enter an angle between an x-axis of micropipette 110 and the true x axis. Because manipulator 108 may be manufactured to hold micropipettes at this angle, the angle does not typically change during operation of autoinjector 100. In some examples, the angle is in a range of 45.2° to 45.4°.

Figure 9:
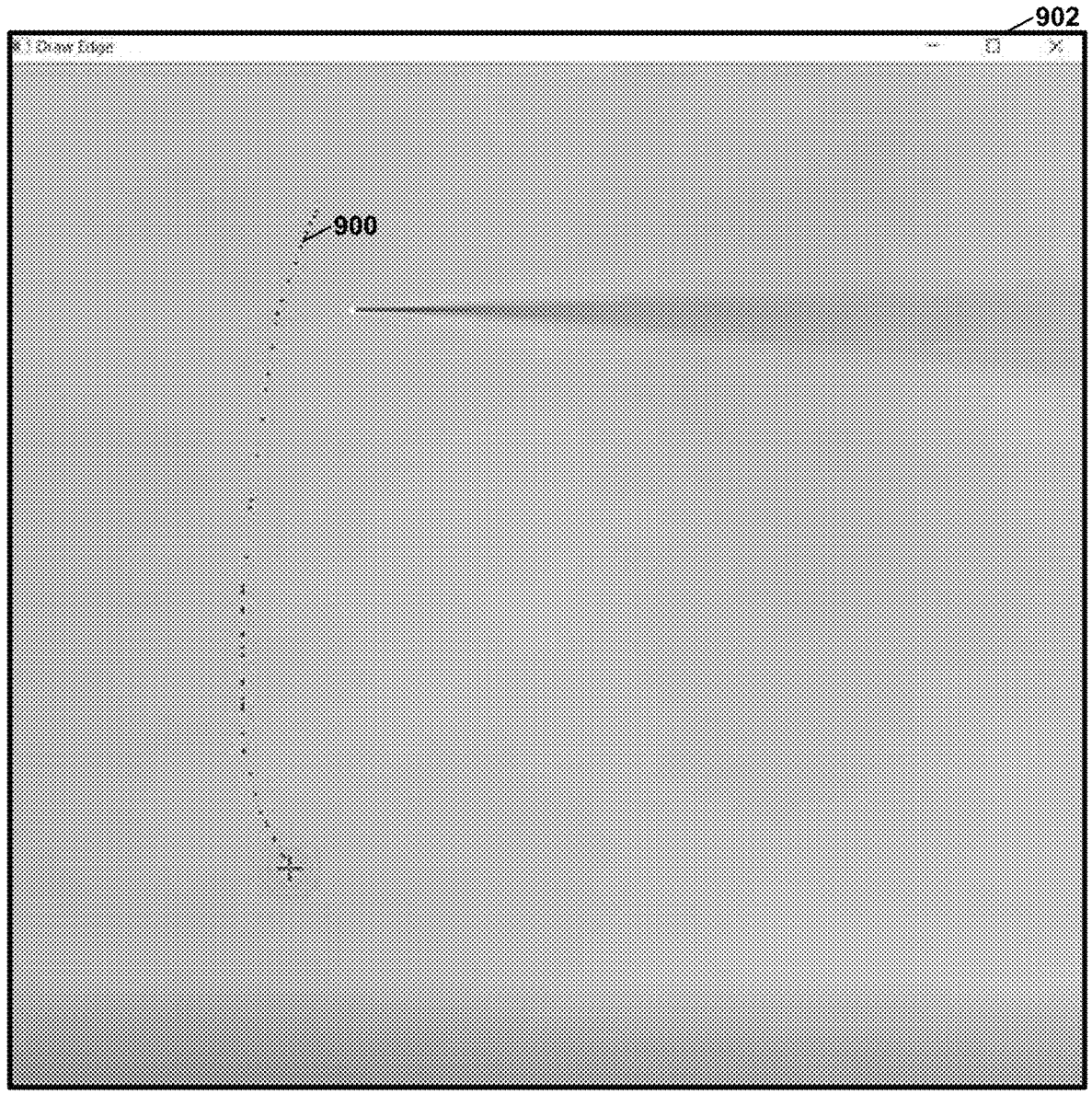
FIG. 9 illustrates an example line traced by the user in a pop-up window generated by the computing device in accordance with a technique of this disclosure.

To test calibration, the user may click the "draw edge" button 430 (FIG. 4B) (834). In response to receiving an indication of user input selecting the "draw edge" button 430, computing device 102 may output a pop-up window for display. The pop-up window includes an image generated by microscope camera 104. The user may then use a cursor to trace a trajectory line in the pop-up window (836). In some examples, computing device 102 may automatically smooth the trajectory line to reduce abrupt corners. After tracing the trajectory line, the user may close the pop-up window. FIG. 9 illustrates an example trajectory line 900 traced by the user in a pop-up window 902 generated by computing device 102 in accordance with a technique of this disclosure. In the example of FIG. 9, trajectory line 900 is shown in black. In some examples, when the user closes the popup window, computing device 102 causes a white line to appear in camera view area 420 where the user has drawn trajectory line 900.

After tracing the trajectory line, the user may move micropipette 110 close to the top of the line (838). The user may use a joystick, knob, or other controller to move micropipette 110. Additionally, the user may enter trajectory parameters into trajectory planning controls 414 (FIG. 4A) or automated microinjection controls 510. As shown in the example FIG. 4C, trajectory planning controls 414 may include an approach distance control 450, a depth control 452, a spacing control 454, a speed control 456, and a number of cells control 458 that allow the user to input an approach distance parameter, a depth parameter, a spacing parameter, a speed parameter, and a number-of-cells parameter, respectively. The approach distance may indicate a distance that micropipette 110 pulls out of the tissue before moving along (e.g., parallel to) the traced trajectory line to the next injection location. In one example, the approach distance may be set to 25 μm. In other examples, the approach distance may be set to 20 μm to 40 μm. The depth parameter indicates a depth that manipulator 108 inserts a tip of micropipette 110 into the tissue. In one example, the depth parameter is set to 15 μm. In other examples, the depth parameter may be set to 10-15 μm for apical progenitors, 30-40 μm for neurons on a basal side of the tissue, or other depths. The spacing parameter indicates a distance along the trajectory line between sequential injections. In one example, the spacing parameter is set to 10-30 μm. The speed parameter is the speed of micropipette 110. In some examples, the speed parameter is expressed as microns/second. Thus, setting the speed parameter to 100 microns/second results in movement of micropipette 110 at 100 microns/second. In such examples, the speed parameter may range from 100% to 1000%. The number-of-cells parameter may indicate how many cells are to be injected. The user may set the number-of-cells parameter to N cells (e.g., 60 cells). In some examples, the number-of-cells parameter can be as large as desired and autoinjector 100 may stop micropipette 110 when it runs out of distance along the trajectory line.

After entering the trajectory parameters, the user may click the "set values" button 462 in the injection controls 416 to set the trajectory parameters (842). Additionally, the user may select the "run trajectory" button 464 (FIG. 4C) to cause autoinjector 100 to start moving micropipette 110 along the trajectory. In other words, computing device 102 may control manipulator 108 to move the tip of micropipette 110 along a path defined by the trajectory line. After autoinjector 100 has finished moving micropipette 110 along the trajectory, computing device 102 may output the number of attempts for display in response monitor 418. The user may observe micropipette 110 in camera view area 420 as micropipette 110 moves along the trajectory and may determine whether the movement of micropipette 110 is satisfactory (846). If the movement of micropipette 110 is not satisfactory ("NO" branch of 846), the user may recalibrate autoinjector 100. For instance, the user may perform actions (822) through (844) again.

On the other hand, if the movement of micropipette 110 is satisfactory ("YES" branch of 846), the user may verify that micropipette 110 is not clogged before instructing autoinjector 100 to perform an actual injection operation (850). In some examples, to verify that micropipette 110 is not clogged, the user may switch the view back to the microscope eyepiece (see actions (806) and (808), switch on an epi-shutter to illuminate the tissue sample, and switch a filter wheel (beneath objectives) to an appropriate illumination wavelength. The appropriate illumination wavelength is a wavelength under which a dye emitted through the tip of micropipette 110 will fluoresce light visible to the user. In examples where an injection solution in micropipette 110 contains a dye, the user should see a small cloud of dye being emitted through the tip of micropipette 110. If the user sees no cloud, the user may increase the pressure (e.g., as in action (808)). If the user increases the pressure (e.g., above 5 pounds per square inch (PSI)) and sees no cloud, micropipette 110 may be clogged. In some instances, to unclog micropipette 110, the user may centrifuge the injection solution and remove only supernatant, replace micropipette 110, and pull micropipette 110 at 1-degree of temperature lower. Lowering the temperature by 1-degree may create a larger opening in micropipette 110, which may prevent clogging.

At this point, the user may reposition tissue sample 114 and search for an appropriate focal plane for injection (852). For instance, the user may reposition tissue sample 114 such that micropipette 110 may inject tissue sample 114. The ideal tissue area for microinjection will have an edge that is sharp within the same focal plane. When the ideal focal plane is found, the user may adjust a position of micropipette 110, draw a trajectory, bring the tip of micropipette 110 close to the top of the trajectory, and then click the tip of micropipette 110. The user may draw the desired trajectory by clicking the "draw edge" button 430 (FIG. 4B) and drawing the desired trajectory in the same manner as described above. Clicking the tip of micropipette 110 may enable computing device 102 to establish a location of the tip of micropipette 110 relative to the trajectory. The user may then select the "run trajectory" button 464 (856).

If at any point the user wishes to stop the process, the user may click the "stop process" button 466. The ideal slice may have several focal planes for injection and the user can repeat steps (844) to (852) for each of the focal planes. Each of the focal planes may correspond to a different depth (e.g., different locations along a z-axis that passes through an aperture of microscope camera 104. After use, the user may pull micropipette 110 out of fluid, remove tissue sample 114, and reposition stage to next slice (i.e., a next tissue sample), if applicable. In some examples, the user does not need to recalibrate micropipette 110 unless the user exchanges micropipettes. In some examples, autoinjector 100 may automatically load another tissue sample. The user may repeat steps (844) to (856) if desired. After the user has completed injections, the user may remove micropipette 110 from the solution, remove slices, and turn off all devices.

Figure 10:
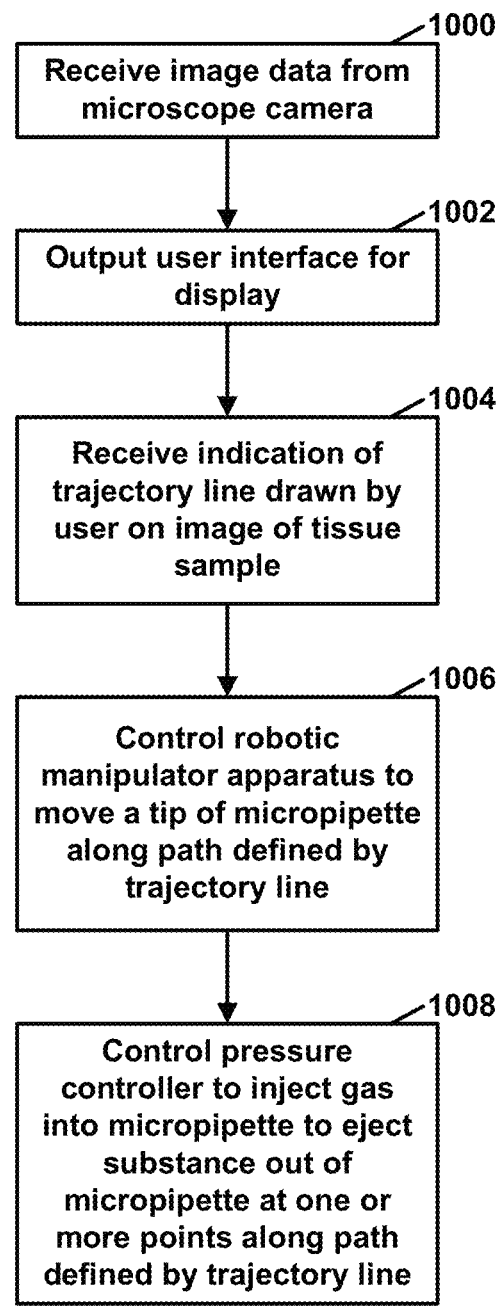
FIG. 10 is a flowchart illustrating an example operation of the autoinjector in accordance with a technique of this disclosure.

FIG. 10 is a flowchart illustrating an example operation of autoinjector 100 in accordance with a technique of this disclosure. In the example of FIG. 10, computing device 102 (FIG. 1) of autoinjector 100 may receive image data from microscope camera 104 (1000). The image data may comprise images of tissue sample 114.

Additionally, computing device 102 may output a user interface for display (1002). The user interface may contain one of the images of tissue sample 114 captured by microscope camera 104. For example, computing device 102 may output GUI 400 (FIG. 4) for display. In some examples, computing device 102 may output a separate GUI (e.g., pop-up window 902 (FIG. 9)).

Additionally, in the example of FIG. 10, computing device 102 may receive an indication of user input of a trajectory of micropipette 110 (1004). For instance, the user interface may include a current image of an injection site received from microscope camera 104, as shown in FIG. 9, and computing device 102 is configured to receive the indication of user input of the trajectory as an indication of the line drawn on the current image data by the user.

Figure 12:
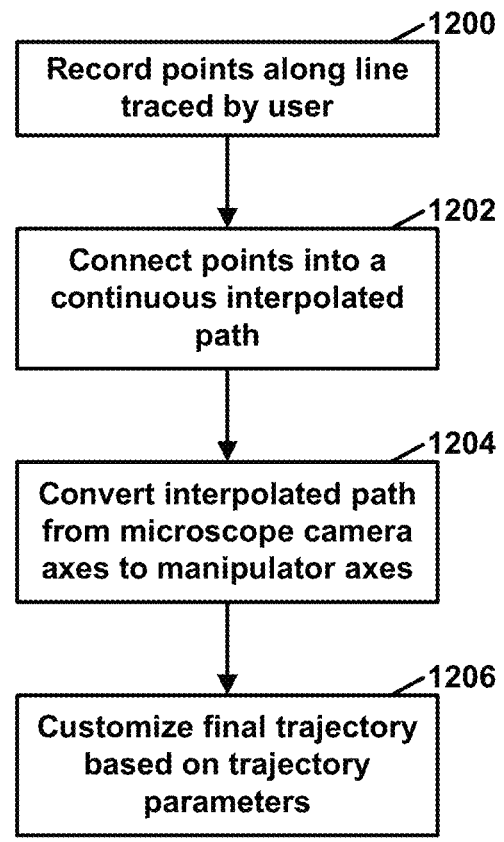
FIG. 12 is a flowchart illustrating an example operation of the computing device to generate a path defined by a trajectory line in accordance with a technique of this disclosure.

Additionally, in the example of FIG. 10, computing device 102 may control manipulator 108 (i.e., a robotic manipulator apparatus) to move a tip of micropipette 110 along a path defined by the trajectory (1006). The light dotted lines in part 306 of FIG. 3 shows one example of a path defined by the trajectory. In some examples, computing device 102 is configured to use image data from microscope camera 104 to control manipulator 108 such that a tip of micropipette 110 moves to positions in accordance with the path defined by the trajectory. Computing device 102 is configured to use image data from microscope camera 104 to control manipulator 108 such that the tip of micropipette 110 moves to positions in accordance with the path defined by trajectory. That is, computing device 102 may map a trajectory line drawn by the user on image data from microscope camera 104 to a frame of reference in the axes of motion of manipulator 108. FIG. 12, explained in detail below, describes an example of such a mapping. As part of using the image data from microscope camera 104 to control manipulator 108, computing device 102 may be configured to use image data from microscope camera 104 to control an injection depth of micropipette 110.

Computing device 102 may also control pressure controller 106 to inject gas into micropipette 110 to eject a substance out of micropipette 110 at one or more points along the path defined by the trajectory line, and thus one or more cells of tissue sample 114 (1008). The one or more points may occur at points on the path defined by the trajectory line where the tip of micropipette 110 reaches the injection depth. Tissue sample 114 may be a sample of any of wide variety of tissue types. For instance, the techniques of this disclosure are not limited to application with respect to tissues of particular species or organs. Computing device

102 may repeat action (1008) at various points along the path to inject multiple the substance into cells of tissue sample 114.

In some examples, in addition to receiving an indication of user input of the trajectory, computing device 102 receives, via the user interface, indications of user input indicating trajectory parameters. For example, computing device 102 may receive, via the user interface (e.g., via depth control 452 (FIG. 4C)), an indication of user input specifying a depth of injection. In this example, computing device 102 may control the robotic manipulator apparatus to insert the tip of micropipette 110 to the specified depth of injection. In some examples, computing device 102 may also receive, via the user interface, indications of user input specifying an approach distance parameter, a spacing parameter, a speed parameter, and a number of cells parameter, as described elsewhere in this disclosure.

Additionally, computing device 102 may receive, via the user interface, indications of user input indicting one or more other parameters. For example, computing device 102 may receive, via the user interface, an indication of user input specifying a pressure (e.g., using manual injection controls 406). In this example, computing device 102 may control pressure controller 106 to inject the gas at the specified pressure. In other words, computing device 102 may control processor controller 106 to pressurize micropipette 110 with a gas to inject a substance out of micropipette 110.

Figure 11:
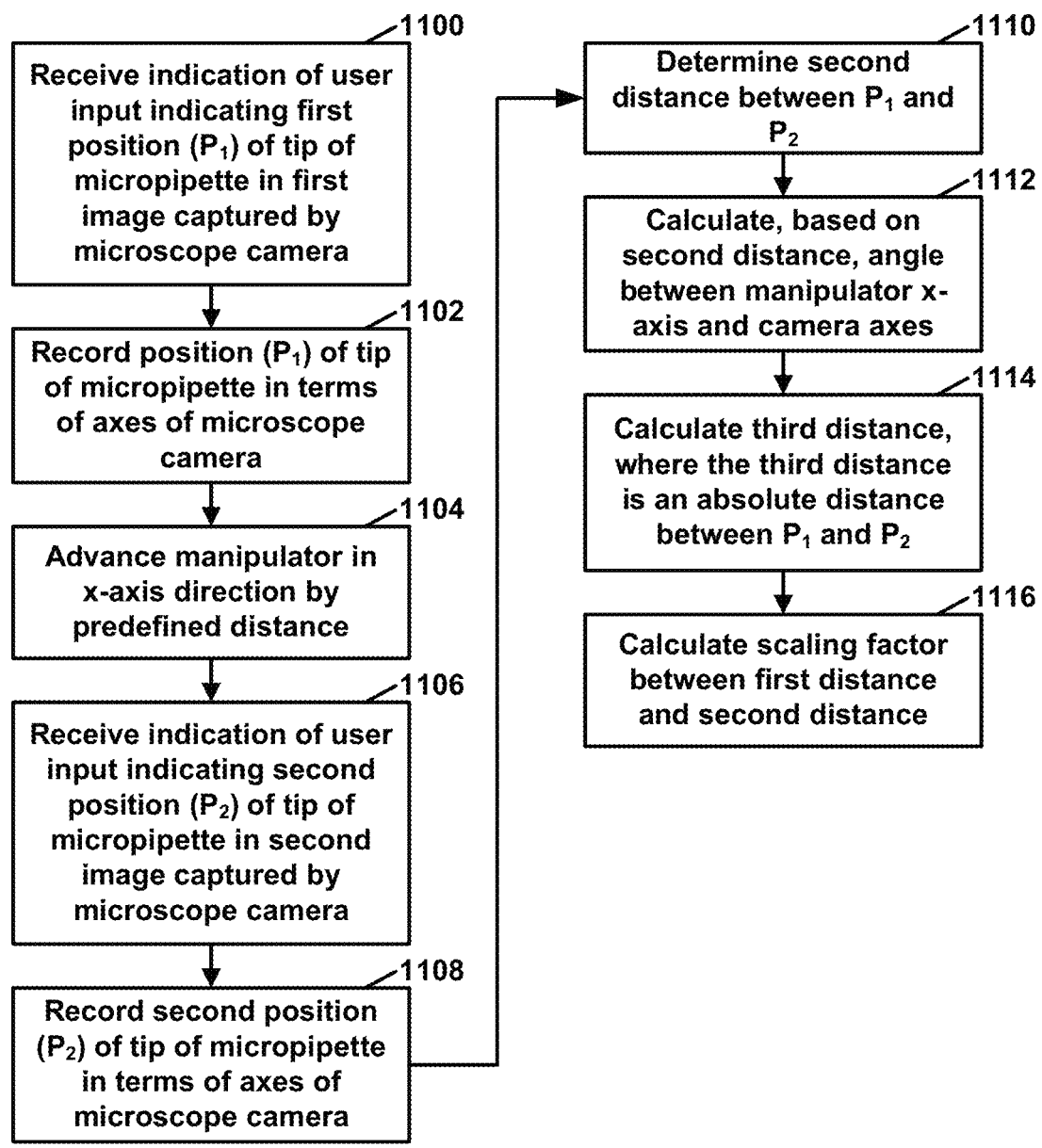
FIG. 11 is a flowchart illustrating an example calibration operation in accordance with a technique of this disclosure.

In some examples, prior to steps (1004) and (1006), autoinjector 100 performs a calibration process. Autoinjector 100 may perform the calibration process in various ways. For example, autoinjector 100 may perform the calibration process in accordance with the examples of FIG. 6A, FIG. 6B, and FIG. 7. In some examples, as part of performing the calibration process, computing device 102 determines a scaling factor and an angle of difference between axes of microscope camera 104 and axes of motion of manipulator 108. In such examples, computing device 102 determines the path defined by the trajectory based on the scaling factor and the angle. FIG. 11, described in detail below, provides an example of how computing device 102 may determine the scaling factor and the angle. FIG. 12, described in detail below, provides an example of how computing device 102 may determine the path defined by the trajectory.

FIG. 11 is a flowchart illustrating an example calibration operation in accordance with a technique of this disclosure. As discussed elsewhere in this disclosure, computing device 102 may use images acquired by microscope camera 104 to guide micropipette 110 in space. Manipulator 108 controls the motion of micropipette 110 and has a coordinate frame in a 3-dimensional cartesian space. To control the motion of micropipette 110 in space using images, computing device 102 may map movement of manipulator 108 in the 3-dimensional cartesian coordinate space to corresponding changes in position of micropipette 110 in the field of view (FOV) of microscope camera 104. This mapping may allow us to guide micropipette 110 to any point in the FOV for targeted microinjection. To do this, autoinjector 100 performs a calibration procedure at the beginning of experiment.

A calibration function is used to enable microscope camera image guided control of micropipette 110. The calibration function may convert points in the camera axes ($C_x$, $C_y$) to points in the manipulator axes ($M_x$, $M_y$). To connect the two coordinate frames, computing device 102 may find an angle offset between the manipulator axes and the camera axes according to the steps shown in the example of FIG. 11.

As shown in the example of FIG. 11, computing device 102 may receive an indication of user input indicating a first position ($P_1$) of the tip of micropipette 110 in a first image captured by microscope camera 104 (1100). For instance, computing device 102 may receive an indication of a mouse click or tap input in the first image at a position that shows the tip of micropipette 110. In response to receiving the indication of user input indicating the first position ($P_1$), computing device 102 may record the first position ($P_1$) of the tip of micropipette 110 in terms of the axes of microscope camera 104 (1102). Computing device 102 may record the position in response to the user indicating the tip of micropipette 110 in action (826) of FIG. 8. The recorded position may be denoted by:

$$P_1(C_x, C_y)$$

Next, computing device 102 may advance manipulator 108 in an x-axis ($M_x$) direction by a predefined first distance (1104). In other words, computing device 102 may control the robotic manipulator apparatus (i.e., manipulator 108) to advance the tip of micropipette in the manipulator x-axis by a predefined first distance. The predefined first distance may be denoted as:

$$|X|$$

Computing device 102 may then receive an indication of user input indicating a second position ($P_2$) of the tip of micropipette 110 in a second image captured by the microscope camera after manipulator 108 has advanced the tip of micropipette 110 in the manipulator x-axis by the predefined first distance (1106). In response to receiving the indication of user input indicating the second position of the tip of micropipette 110 in the second image, computing device 102 may record the second position ($P_2$) of the tip of micropipette 110 in terms of the axes of microscope camera 104 (1108). The recorded second position may be denoted by:

$$P_2(C_x, C_y)$$

Furthermore, in the example of FIG. 11, computing device 102 may calculate a distance between $P_1$ and $P_2$ (i.e., a second distance) (1110). For instance, computing device 102 may calculate the distance between $P_1$ and $P_2$ as:

$$D(C_x, C_y) = |P_1(C_x, C_y) - P_2(C_x, C_y)| \tag{1}$$

where:

$$D(C_x, C_y) = \begin{bmatrix} D(C_x) \\ D(C_y) \end{bmatrix}$$

Computing device 102 may then calculate, based on the second distance, an angle between the manipulator x-axis ($M_x$) and the camera axes ($C_x$, $C_y$) (1112). In other words, computing device 102 may calculate, based on the second distance, the angle between the axes of microscope camera 104 and axes of motion of manipulator 108. For instance, computing device 102 may calculate the angle between the manipulator x-axis ($M_x$) and the camera axes ($C_x$, $C_y$) as follows:

$$\theta = \arctan \frac{D(C_x)}{D(C_y)} \tag{2}$$

Furthermore, computing device 102 may calculate a third distance (D), where the third distance is an absolute distance between $P_1$ and $P_2$ (1114). That is, the third distance is a distance between $P_1$ and $P_2$ expressed in terms of manipulator axes. For instance, computing device 102 may calculate the third distance (D) between $P_1$ and $P_2$ as follows:

$$D=\sqrt{D(C_x)^2+D(C_y)^2} \quad (3)$$

Additionally, computing device 102 may calculate a scaling factor (S) as a ratio between the first distance and the second distance (1116). For instance, computing device 102 may calculate the scaling factor as:

$$S = \frac{D}{|X|} \quad (4)$$

In the example of FIG. 11, the equations computing device 102 may use to relate the camera axes to the manipulator axes may be given by:

$$\begin{bmatrix} C_x \\ C_y \end{bmatrix} = R(\theta) \cdot \begin{bmatrix} M_x \\ M_y \end{bmatrix} \quad (5)$$

$$\begin{bmatrix} M_x \\ M_y \end{bmatrix} = R^{-1}(\theta) \cdot \begin{bmatrix} C_x \\ C_y \end{bmatrix} \quad (6)$$

where $$R(\theta) = \begin{bmatrix} -S \cdot \cos\theta & S \cdot \sin\theta \\ -S \cdot \sin\theta & -S \cdot \cos\theta \end{bmatrix}$$

$$R^{-1}(\theta) = \frac{1}{S^2} \begin{bmatrix} -S \cdot \cos\theta & -S \cdot \sin\theta \\ S \cdot \sin\theta & -S \cdot \cos\theta \end{bmatrix}$$

Computing device 102 may solve for the manipulator axes in terms of the camera axes in term of the following equations:

$$\begin{bmatrix} M_x \\ M_y \end{bmatrix} = R^{-1}(\theta) \cdot \begin{bmatrix} C_x \\ C_y \end{bmatrix} \quad (7)$$

$$\begin{bmatrix} M_x \\ M_y \end{bmatrix} = \frac{1}{S^2} \begin{bmatrix} -S \cdot \cos\theta & -S \cdot \sin\theta \\ S \cdot \sin\theta & -S \cdot \cos\theta \end{bmatrix} \begin{bmatrix} C_x \\ C_y \end{bmatrix} \quad (8)$$

$$\begin{bmatrix} M_x \\ M_y \end{bmatrix} = \begin{bmatrix} \frac{1}{S} \cdot (-C_x \cdot \cos\theta - C_y \cdot \sin\theta) \\ \frac{1}{S} \cdot (C_x \cdot \sin\theta - C_y \cdot \cos\theta) \end{bmatrix} \quad (9)$$

$$M_x = \frac{1}{S} \cdot (-C_x \cdot \cos\theta - C_y \cdot \sin\theta) \quad (10)$$

$$M_y = \frac{1}{S} \cdot (C_x \cdot \sin\theta - C_y \cdot \cos\theta) \quad (11)$$

Using these equations, computing device 102 may convert any point in the camera axes ($C_x$, $C_y$) to a point in the manipulator axes ($M_x$, $M_y$) for image guided position control of the injection micropipette 110.

FIG. 12 is a flowchart illustrating an example operation of computing device 102 to generate a path defined by a trajectory line in accordance with a technique of this disclosure. Customization of the microinjection procedure may be important for optimizing parameters and tuning the microinjection for different applications and different tissue sample types based on the users' needs. Thus, autoinjector 100 may be designed to take in user-defined parameters and output a customized trajectory of microinjection.

As discussed above, the autoinjector software may allow the user to define a path of microinjection, and to customize the trajectory of microinjection using trajectory parameters. The trajectory parameters may include the depth micropipette 110 is inserted into tissue during microinjection, denoted D, the distance micropipette 110 pulls out of the tissue after microinjection attempts, denoted A, the spacing along the path between subsequent microinjection attempts, denoted S, the speed micropipette 110 is inserted into the tissue during the whole procedure, and the constant pressure applied to micropipette 110 used to prevent clogging, also referred as compensation pressure. The defined path of microinjection and parameters are used to generate a trajectory of micropipette 110 following calibration. Computing device 102 may generate the final trajectory according to the protocol described in FIG. 12.

In the example of FIG. 12, computing device 102 receives indications of user input of a line (i.e., a trajectory line) drawn using a cursor on a microscope image along a desired path of microinjection. As the user drags the cursor, computing device 102 may record a set of points at different pixels along this line (1200). Each of the points may be denoted as:

$$t(C_x, C_y)$$

Next, computing device 102 may connect the points into a continuous interpolated path (1202). In some examples, computing device 102 may use univariate spline interpolation to connect the points into the continuous path so that the line is defined for every pixel along the path. This may ensure that movements of manipulator 108 achieve the highest resolution possible as limited by the resolution of the pixels within images of microscope camera 104. In the example of FIG. 12, the interpolated path as expressed in the microscope camera axes may be denoted $T(C_x, C_y)$:

$$T(C_x, C_y) = \begin{bmatrix} T(C_x) \\ T(C_y) \end{bmatrix}$$

Computing device 102 may then convert the interpolated path from the microscope camera axes to manipulator axes (1204). The interpolated path as expressed in the manipulator axes may be denoted $T(M_x, M_y)$:

$$T(M_x, M_y) = \begin{bmatrix} T(M_x) \\ T(M_y) \end{bmatrix}$$

Computing device 102 may convert the interpolated path using the calibration matrix, $R(\theta)$, described above with respect to FIG. 11, where $\theta$ is the angle offset between manipulator axes and camera axes found during calibrations. Computing device 102 may solve for $T(M_x, M_y)$ using the following system of equations:

$$\begin{bmatrix} T(M_x) \\ T(M_y) \end{bmatrix} = R^{-1}(\theta) \cdot \begin{bmatrix} T(C_x) \\ T(C_y) \end{bmatrix} \quad (12)$$

$$\begin{bmatrix} T(M_x) \\ T(M_y) \end{bmatrix} = \begin{bmatrix} \frac{1}{S} \cdot (-T(C_x) \cdot \cos\theta - T(C_y) \cdot \sin\theta) \\ \frac{1}{S} \cdot (T(C_x) \cdot \sin\theta - T(C_y) \cdot \cos\theta) \end{bmatrix} \quad (13)$$

$$\begin{bmatrix} T(M_x) \\ T(M_y) \end{bmatrix} = \frac{1}{S^2} \begin{bmatrix} -S \cdot \cos\theta & -S \cdot \sin\theta \\ S \cdot \sin\theta & -S \cdot \cos\theta \end{bmatrix} \cdot \begin{bmatrix} T(C_x) \\ T(C_y) \end{bmatrix} \quad (14)$$

$$T(M_x) = \frac{1}{S} \cdot (-T(C_x) \cdot \cos\theta - T(C_y) \cdot \sin\theta) \quad (15)$$

-continued $$T(M_y) = \frac{1}{S} \cdot (T(C_x) \cdot \sin\theta - T(C_y) \cdot \cos\theta) \quad (16)$$

Additionally, computing device 102 may customize the final trajectory (i.e., the path defined by the trajectory line) based on the trajectory parameters input by the user (1206). The coordinates for each injection may be given by:

$$T_i(M_x, M_y) = \begin{bmatrix} T_1(M_x, M_y) \\ T_2(M_x, M_y) \\ \dots \\ T_{N-1}(M_x, M_y) \\ T_N(M_x, M_y) \end{bmatrix} \quad (17)$$

where i is defined as:

$\{i \in \mathbb{Z} \mid 1 \leq i \leq N\}$ where N is the total number of injection attempts. In these equations, i is an index of an individual injection. For each value of i, computing device 102 may generate the trajectory as follows. Autoinjector 100 moves micropipette 110 to the first position:

$T_i(M_x, M_y)$

Autoinjector 100 may advance micropipette 110 by:

$T_i(M_x+D, M_y)$ where D is the depth of injection, and pulled out of tissue a distance to a location:

$T_i(M_x-D-A, M_y)$ where A is the approach distance specified by the user. Next, computing device 102 may advance micropipette 110 to the next injection site:

$T_i(M_x-D-A, M_y-S)$ where S is the spacing between injections specified by the user. Computing device 102 may repeat this until micropipette 110 has reached the end of the trajectory.

Thus, computing device 102 may receive an indication of user input of a trajectory as an indication of a line traced on a current image by the user. In this example, the current image is an image of the tissue sample captured by microscope camera 104. In response to receiving the indication of user input of the trajectory, computing device 102 may record points along the line traced on the current image data by the user. In this example, computing device 102 may be configured such that, as part of determining the path defined by the trajectory based on the scaling factor and the angle, computing device 102 may connect the points into a continuous interpolated path. Additionally, computing device 102 may convert, based on the scaling factor and the angle, the continuous interpolated path from the microscope camera axes to the manipulator axes. After converting the continuous interpolated path, computing device 102 may customize the continuous interpolated path based on trajectory parameters.

Various experiments were performed to test the utility of autoinjector 100. For example, in one experiment, the effects of pressure and injection depth on yield were investigated using A488 on 400 micron thick coronal slices of the mouse telencephalon that are 14.5 days old from conception (E14.5) and it was found that optimal injection success occurred using 75 mbar and 15 micron depth. It was observed that the tissue quality influenced yield.

To compare manual microinjection for a new and experienced user, a manual microinjection station was used to inject dextran coupled with alexa-488 into the ventral side of a mouse telencephalon in E14.5 400 micron thick coronal slices followed by immediate fixation and immunohistochemistry (IHC). It was found that manual injection had a success rate (as determined by 4',6-diamidino-2-phenylindole (DAPI) overlap with A488 and apical attachment) of (preliminary data suggests 0-3%, n=2, 30 attempts, total time=190 s) for a new user and (preliminary data suggests 10%, n=1, 30 attempts, total time=150 s) for an experienced user after 0 hours of cell culture. This represents a successful injection rate of 0-0.28 injections per minute for a new user and 1.2 successful injections per minute for an experienced user. For automated microinjection, it was found that 43.7+/−9.1% of attempts resulted in injections and 33.3+/−6.8% resulted in minimal cell damage (determined by DAPI overlap with A488 and apical attachment) (205+/−80 attempts, n=4, total time=315 s), with a rate of 12.89 successful injections per minute. Thus, in this experiment, autoinjector 100 enabled a 46× fold increase in efficiency relative to a new user on the manual system and a 10× fold increase in injection efficiency relative to an experienced user on the manual system.

In one experiment involving organotypic slices of developing mouse and human telencephalons using dye and mRNA of genes of interest, 44% of attempts resulted in successful injections. Other uses may analyze the confocal data to further quantify the efficiency of injection in these models. Additionally, it was demonstrated that autoinjector 100 had the ability to inject tissues from other models (e.g., ferret, human), and tissues from other regions of the body (e.g., epithelial).

In some experiments, it was demonstrated that autoinjector 100 significantly increased the yield of injection relative to manual use (10-46-fold increase), does not significantly affect viability over 0, 24, and 48 hours in culture, enables mRNA translation, allows for targeting of various epithelial tissues, and can be applied to other model organisms, including human, ferret, and brain organoids. Autoinjector 100 thus may open doors to new types of experiments previously inhibited by the amount of effort required to implement including investigating effects of mRNA concentration, composition on cell fate and tracking these effects on cell reprogramming and lineage.

To explore viability of targeted cells, dextran coupled with A488 was injected into E14.5 400 micron thick coronal slices of a mouse telencephalon and quantified cell fluorescence and morphology via IHC after 24, or 48 hours post injection. After 24 hours of culture, 38% of total attempted injections resulted in injected cells (as determined by DAPI overlap with A488). Of the injected cells, 44% had apical attachments.

To explore the potential of injected cells to translate mRNA, the mRNA of red fluorescent protein (RFP) was injected along with dextran coupled to alexa 488 and cells were cultured for 24, or 48 hours, followed by fixation and IHC. Due to the high concentration of RFP and subsequent increased viscosity of the solution, it was observed that it may be necessary to raise the pressure to 145 mbar to observe similar fluorescent output of the pipette solution. It was also noticed that after an hour after centrifuging the injection combination and using only supernatant, the mRNA products began to aggregate again and it was necessary to re-centrifuge and also to increase pipette size by lowering the pipette puller by 1 degree C.

Experiments have shown that autoinjector 100 may be generalizable to various types of tissues (e.g., autoinjector 100 works in various locations) and with various types of model organisms (e.g., autoinjector 100 works for other organisms).

Microinjection serves as a unique tool to precisely control concentration and complexity of gene product injected into single cells. Until now, microinjection for use in neural stem cell lineage tracking was extremely difficult to perform manually which limited its use in developmental biology. It was demonstrated that the repetitive mechanics of injection could be captured by an automated algorithm and increase yield of injection as well as decrease time of injection procedure relative to manual injections resulting in a 46×, and 10× fold increase in performance for a new or experienced user on the manual injection platform, respectively. The resulting rate using autoinjector 100 of 12 successful injections per minute relative to 0.28 or 1.2 injections per minute manually represents a significant increase in performance that may reduce the effort required to perform complex experiments. It was also verified that injected cells can survive 24 hours of culture and express injected mRNA. Furthermore, the generalizability of the techniques of this disclosure to various tissues and model organisms was demonstrated. The increased ease of use coupled with the generalizability and gene product capabilities of the automated microinjection platform may enable broad uptake of the microinjection technique and may allow for new experiments in the realm of cell tracking across diverse fields in biology.

Additionally, autoinjector 100 may be paired with other single cell techniques upon further optimization including live imaging, tracking migration, and mRNA barcoding. The throughput enabled by autoinjector 100 may make lineage tracing studies realistically possible. For instance, the advent of stem cell engineered tissue, 3D printed organs may have huge commercial potential. Extending autoinjector 100 to gene manipulation of the such tissues with cellular resolution may be very powerful. Overall, the customization of injection fluid and can open the door to new types of experiments previously inhibited by the amount of effort required to implement including investigating effects of mRNA concentration, composition on cell fate and tracking these effects on cell reprogramming and lineage.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Various examples have been described. These and other examples are within the scope of the following claims.

The invention claimed is:

1. A system for injecting a substance into cells of a tissue sample, the system comprising:
   a robotic manipulator apparatus configured to hold and position a micropipette;
   a pressure controller;
   a microscope camera; and
   a computing device configured to:
      receive image data from the microscope camera, wherein the image data comprises an image of the tissue sample;
      output a user interface for display, wherein the user interface contains the image of the tissue sample;
      receive, via the user interface, an indication of a trajectory line drawn by a user on the image of the tissue sample;
      control the robotic manipulator apparatus to move a tip of the micropipette along a path defined by the trajectory line; and
      control the pressure controller to inject a gas into the micropipette to eject the substance out of the micropipette at one or more points along the path defined by the trajectory line.

2. The system of claim 1, wherein the tissue sample comprises an intact tissue.

3. The system of claim 1, wherein the computing device is further configured to:
   receive, via the user interface, an indication of user input specifying a pressure; and
   control the pressure controller to inject the gas at the specified pressure.

4. The system of claim 1, wherein the computing device is further configured to:
   receive, via the user interface, an indication of user input specifying a depth of injection; and
   control the robotic manipulator apparatus to insert the tip of the micropipette to the specified depth of injection.

5. The system of claim 1, wherein the computing device is configured to use the image data from the microscope camera to control the robotic manipulator apparatus such that the tip of the micropipette moves to positions in accordance with the path defined by the trajectory line.

6. The system of claim 1, wherein the computing device is configured to use the image data from the microscope camera to control an injection depth of the micropipette.

7. The system of claim 1, wherein the computing device is further configured to:
perform a calibration process that determines a scaling factor and an angle of difference between axes of the microscope camera and axes of motion of the robotic manipulator apparatus; and
determine the path defined by the trajectory line based on the scaling factor and the angle.

8. The system of claim 7, wherein:
the axes of motion of the robotic manipulator apparatus include a manipulator x-axis and a manipulatory-axis,
the computing device is configured such that, as part of performing the calibration process, the computing device:
receives an indication of user input indicating a first position of the tip of the micropipette in a first image captured by the microscope camera;
in response to receiving the indication of user input indicating the first position of the tip of the micropipette in the first image, records the first position of the tip of the micropipette in terms of the axes of the microscope camera;
controls the robotic manipulator apparatus to advance the tip of the micropipette in the manipulator x-axis by a predefined first distance;
receives an indication of user input indicating a second position of the tip of the micropipette in a second image captured by the microscope camera after the robotic manipulator apparatus has advanced the tip of the micropipette in the manipulator x-axis by the predefined first distance;
in response to receiving the indication of user input indicating the second position of the tip of the micropipette in the second image, records the second position of the tip of the micropipette in terms of the axes of the microscope camera;
determines a second distance, the second distance being between the first position and the second position;
calculates, based on the second distance, the angle of difference between the axes of the microscope camera and the axes of motion of the robotic manipulator apparatus;
calculates a third distance, the third distance being an absolute distance between the first position and the second position; and
calculates the scaling factor a ratio of the first distance and the third distance.

9. The system of claim 7, wherein:
the computing device is configured to, in response to receiving the indication of user input of the trajectory line, record points along the trajectory line, and
the computing device is configured such that, as part of determining the path defined by the trajectory line based on the scaling factor and the angle, the computing device:
connects the points into a continuous interpolated path;
converts, based on the scaling factor and the angle, the continuous interpolated path from the axes of the microscope camera to the manipulator axes; and
after converting the continuous interpolated path, customizes the continuous interpolated path based on trajectory parameters.

10. A method performed by a system for injecting a substance into cells of a tissue sample, the method comprising:
receiving image data from a microscope camera, wherein the image data comprises an image of the tissue sample;
outputting a user interface for display, wherein the user interface contains the image of the tissue sample;
receiving, via the user interface, an indication of user input of a trajectory line drawn by a user on the image of the tissue sample;
controlling a robotic manipulator apparatus to move a tip of a micropipette along a path defined by the trajectory line; and
controlling a pressure controller to inject a gas into the micropipette to eject the substance out of the micropipette at one or more points along the path defined by the trajectory line.

11. The method of claim 10, wherein the tissue sample comprises an intact tissue.

12. The method of claim 10, further comprising:
receiving, via the user interface, an indication of user input specifying a pressure; and
controlling the pressure controller to inject the gas at the specified pressure.

13. The method of claim 10, further comprising:
receiving, via the user interface, an indication of user input specifying a depth of injection; and
controlling the robotic manipulator apparatus to insert the tip of the micropipette to the specified depth of injection.

14. The method of claim 10, further comprising:
performing a calibration process that determines a scaling factor and an angle of difference between axes of the microscope camera and axes of motion of the robotic manipulator apparatus; and
determining the path defined by the trajectory line based on the scaling factor and the angle.

15. The method of claim 14, wherein:
the axes of motion of the robotic manipulator apparatus include a manipulator x-axis and a manipulatory-axis,
performing the calibration process comprises:
receiving an indication of user input indicating a first position of the tip of the micropipette in a first image captured by the microscope camera;
in response to receiving the indication of user input indicating the first position of the tip of the micropipette in the first image, recording the first position of the tip of the micropipette in terms of the axes of the microscope camera;
controlling the robotic manipulator apparatus to advance the tip of the micropipette in the manipulator x-axis by a predefined first distance;
receiving an indication of user input indicating a second position of the tip of the micropipette in a second image captured by the microscope camera after the robotic manipulator apparatus has advanced the tip of the micropipette in the manipulator x-axis by the predefined first distance;
in response to receiving the indication of user input indicating the second position of the tip of the micropipette in the second image, recording the second position of the tip of the micropipette in terms of the axes of the microscope camera;
determining a second distance, the second distance being between the first position and the second position;

calculating, based on the second distance, the angle of difference between the axes of the microscope camera and the axes of motion of the robotic manipulator apparatus;

calculating a third distance, the third distance being an absolute distance between the first position and the second position; and calculating the scaling factor as a ratio between the first distance and the third distance.

16. The method of claim 14, wherein:

the method further comprises, in response to receiving the indication of user input of the trajectory line, recording points along the trajectory line, determining the path defined by the trajectory line based on the scaling factor and the angle comprises:

connecting the points into a continuous interpolated path;

converting, based on the scaling factor and the angle, the continuous interpolated path from the axes of the microscope camera to the manipulator axes; and after converting the continuous interpolated path, customizing the continuous interpolated path based on trajectory parameters.

17. A non-transitory computer-readable storage medium having instructions stored thereon that, when executed, cause a computing device of an autoinjector system to:

receive image data from a microscope camera, wherein the image data comprises an image of a tissue sample;

output a user interface for display, wherein the user interface contains the image of the tissue sample;

receive, via the user interface, an indication of user input of a trajectory line drawn by a user on the image of the tissue sample;

control a robotic manipulator apparatus to move a tip of a micropipette along a path defined by the trajectory line; and control a pressure controller to inject a gas into the micropipette to eject a substance out of the micropipette at one or more points along the path defined by the trajectory line.

18. The non-transitory computer-readable data storage medium of claim 17, wherein:

axes of motion of the robotic manipulator apparatus include a manipulator x-axis and a manipulatory-axis, as part of causing the computing device to perform the calibration process, execution of the instructions causes the computing device to:

receive an indication of user input indicating a first position of the tip of the micropipette in a first image captured by a microscope camera of the autoinjector system;

in response to receiving the indication of user input indicating the first position of the tip of the micropipette in the first image, record the first position of the tip of the micropipette in terms of the axes of the microscope camera;

control the robotic manipulator apparatus to advance the tip of the micropipette in the manipulator x-axis by a predefined first distance;

receive an indication of user input indicating a second position of the tip of the micropipette in a second image captured by the microscope camera after the robotic manipulator apparatus has advanced the tip of the micropipette in the manipulator x-axis by the predefined first distance;

in response to receiving the indication of user input indicating the second position of the tip of the micropipette in the second image, record the second position of the tip of the micropipette in terms of the axes of the microscope camera;

determine a second distance, the second distance being between the first position and the second position;

calculate, based on the second distance, an angle of difference between the axes of the microscope camera and the axes of motion of the robotic manipulator apparatus;

calculate a third distance, the third distance being an absolute distance between the first position and the second position; and calculate a scaling factor as a ratio between the first distance and the third distance, wherein the instructions further cause the computing device to:

in response to receiving the indication of user input of the trajectory line, record points along the line traced on the current image by the user;

connect the points into a continuous interpolated path;

convert, based on the scaling factor and the angle, the continuous interpolated path from the axes of the microscope camera to the manipulator axes; and after converting the continuous interpolated path, customize the continuous interpolated path based on trajectory parameters.

* * * * *